United States Patent [19]

Shibano et al.

[11] Patent Number: 5,453,371
[45] Date of Patent: Sep. 26, 1995

[54] BACTERIAL COLLAGENASE GENE OF VIBRIO ALGINOLYTICUS

[75] Inventors: Yuji Shibano, Toyonaka; Kazuyuki Morihara, Shimonoseki; Kenji Okuda, Yokohama; Jun Fukushima, Tokyo, all of Japan

[73] Assignee: Suntory Limited, Osaka, Japan

[21] Appl. No.: 618,946

[22] Filed: Nov. 27, 1990

[30] Foreign Application Priority Data

Nov. 28, 1989 [JP] Japan .................................. 1-308235
Sep. 14, 1990 [JP] Japan .................................. 2-244562

[51] Int. Cl.$^6$ .......................... C12N 9/52; C12N 15/57; C12N 15/70
[52] U.S. Cl. .................. 435/220; 435/69.1; 435/172.3; 435/252.33; 435/320.1; 536/23.2; 935/14; 935/29; 935/73
[58] Field of Search ................. 435/69.1, 172.3, 435/252.3, 320.1, 219, 220, 69.1, 252.33, 320.1; 536/23.2

[56] References Cited

U.S. PATENT DOCUMENTS

| | | | |
|---|---|---|---|
| 4,760,025 | 7/1988 | Estell et al. | 435/222 |
| 4,966,846 | 10/1990 | Deutch et al. | 435/172.3 |
| 5,145,681 | 9/1992 | Fortney et al. | 424/94.63 |
| 5,177,017 | 1/1993 | Lin et al. | 435/252.33 |

FOREIGN PATENT DOCUMENTS

| | | | |
|---|---|---|---|
| 115974 | 8/1984 | European Pat. Off. | 435/220 |
| 309879 | 4/1989 | European Pat. Off. | 435/172.3 |

OTHER PUBLICATIONS

Biochimica Et Biophysica Acta, vol. 874, No. 3, 1986, pp. 296–304.
Gene, vol. 76, 1989, pp. 281–288.
Biochimica Et Biophysica Acta, vol. 522, No. 1, 1978, pp. 218–222.
Chemical Abstracts, vol. 85, 1976, p. 216, abstract No. 58688b.
Hare, P., et al., 1983, Journal of General Microbiology, 129:1141–1147.
Young, R. A., et al., 1983, Science, 222:778–782.
Taylor, M. J., et al., 1979, Advances in Applied Microbiology, 25:7–35.
Fukushima, J., et al., 1989, Journal of Bacteriology, 171(3):1698–1704.
Atsumi, Y., et al., 1989, Journal of Bacteriology 171(9): 5173–5175.
Pharmacia Cabalogne, 1986, p. 60.

*Primary Examiner*—Robert A. Wax
*Assistant Examiner*—William W. Moore
*Attorney, Agent, or Firm*—Wenderoth, Lind & Ponack

[57] ABSTRACT

A collagenase gene derived from bacteria of the species *Vibrio alginolyticus* is disclosed. A recombinant vector containing the gene, a host cell transformed with a plasmid containing the gene and a process for the production of a collagenase by using the host cells are also disclosed.

22 Claims, 10 Drawing Sheets

FIG. 2A

```
1    G ATC GTA CCA GTC ATT ATA TCT GCT GCT GCG ATG TAC TTT TTC TAC ACA CGC CTT GGC    58
59   TTA TCA CAA ACT TAT CTA GGC GTC ATT TTG GCA CAC GCT TTA GGT ACG CCT TTT GTC     118
119  GTC ATT ACC GTT ACT GCG ACG TTA AGT GGC TTT GAC CAT AGC TTG GTA AAA GCG GCT     178
179  AGC TTA GGA GCA AAC CCT GTT TAT ACT TTC AGA CAC ATT ACC TTT AAG CTG CGT CCG     238
239  GGG ATG ATT TCT GGC GGC TTG TTT GCC TTT GAG CAT CGT TCG ACG AGG TTG TGG CGT     298
299  TAT TCC TGA CTG GGG CAG AAC AAA AAA CCG TTC CGA GGC AGA TGT GGT CAG GAA TTC GAG 358
359  AGC AAA TTA GTC CGA CCA TAT TGG CGG TCG CTA CGT TGT TGA TTT TTA TGT CGG TGT GTT 418
419  TGC TCG TGA CGT TAG AAG TTT TCT ATG ACT ATG CAC TTT TTT TGT GTT TGT CGG TTG AAT AAT
478  AAC CAG ACT TTT GCC TTA TTG TTG GTC ACT GCG CTT TTC TTT TGT TTA GGG GCA CCT CAA TTT TTG
538  ACC AAA GGC TTA TAG GCG CTT ATG CCA GCC TCG AAA CGT GCC CAG CGA TGA CTG ACA
598  TGT CAC TCT TGT AGC TTA ATG TCG TGC TCG AAA AGG GAC TTG TTC GAT
658  TGC TGA TAC CAA CTA GCT GGC ATG TTT GGT TTA AGT CGG GCT TTT TCA TCC TTG CTA ATC     718
```

FIG. 2B

```
719  ACA ACA TAG TGT AAA AAT GCA TCA AGT GTG CCC ATC ACG TCA AAC GTC ATT TCC CCA  778
779  CCT TTG CTG ATG GTT TTC AAT AAT CCA ACG ACG GCT TCC TCA GGG ACT AAC GGT TCA ACC  838
839  ACC GCG TTT TTT CGC TCT TTT ATT GAT GTT GAA GCG GGC AGG TTT GCA CGT GCC GTC TCC  898
899  CAG CAA ACT TTG TTG GTT TTA CTG ACA AGG TTG TGC TTG TAG CAG TAG TAA CTG AAT AAA  958
959  AAG CGT GGC AGA TTT TGC CAG CGT TCG GCT TGG ACT TCT AAC CAA AGG TGT AGC TCA 1018
1019 ATA TCA GCG TCG GTC ATA GGA GTT GTT TAG CAA AAA GAA AAG AAA CCA TTT TAT CGC TTT 1078
1079 TGT GAG GAG CAA TAA AAG ATA TCT GGC AAG CCC GTG CAA CGC AAC TCG AGT ACC AAA AAC TGA TAC 1138
1139 TAA AGC AAA TAG ATT TCT GGC TTG TTA ACA AAA TGT TTC TTC TTG TCT TGC GAG TAG ATT ATA TGG AGA 1198
1199 CGC CAC ATT CGG TTG TTA ACA AAA TGT GGC GAT GCA AAA GAC GTA ATG CAT CTA AGG AAA ACT 1258
1259 TGC TCT TGC AGT AAT AAG GGC AGT GGC GAT GCA AAA GAC GTA ATG CAT CTA AGG AAA ACT 1258
1319 CAA TAT AGA AGA AAT TAG ATG GAA CTG AAG ATT TTG AGT GTC GCG ATT GCG ACA ACA TTA 1378
  1                             Met Glu Leu Lys Ile Leu Ser Val Ala Ile Ala Thr Thr Leu   14
1379 ACC AGC ACT GGC GTA TTT GCG TTA AGC GAG CCA GTT TCT CAA GTT ACA GAG CAA CAT GCA 1438
  15 Thr Ser Thr Gly Val Phe Ala Leu Ser Glu Pro Val Ser Gln Val Thr Glu Gln His Ala   34
```

FIG. 2C

```
1439 CAT TCG GCT CAT ACA CAC GGT GTT GAA TTC AAT CGA GTT GAA TAC CAA CCA ACC GCA ACT 1498
  35 His Ser Ala His Thr His Gly Val Glu Phe Asn Arg Val Glu Tyr Gln Pro Thr Ala Thr  54

1499 CTC CCA ATT CAG CCC TCT AAG GCA ACT CGA GTA CAG TCA CTT GAA AGC CTT GAT GAG TCG 1558
  55 Leu Pro Ile Gln Pro Ser Lys Ala Thr Arg Val Gln Ser Leu Glu Ser Leu Asp Glu Ser  74

1559 AGC ACT GCT TGT GAT TTG GAG GCA TTG GTT ACC GAA AGC AGT AAC CAA TTG ATC AGC GAA 1618
  75 Ser Thr Ala Cys Asp Leu Glu Ala Leu Val Thr Glu Ser Ser Asn Gln Leu Ile Ser Glu  94
            70kd N

1619 ATT TTA AGT CAG GGC GCG ACG TGT GTG AAC CAG TTA TTC TCT GCT GAA AGT CGG ATT CAA 1678
  95 Ile Leu Ser Gln Gly Ala Thr Cys Val Asn Gln Leu Phe Ser Ala Glu Ser Arg Ile Gln 114

1679 GAG TCG GTA TTT AGC TCC GAT CAT ATG TAC AAT ATC GCT AAG CAC ACT ACG TTG GCG 1738
 115 Glu Ser Val Phe Ser Ser Asp His Met Tyr Asn Ile Ala Lys His Thr Thr Leu Ala 134

1739 AAG GGG TAT ACG GGT GGC GGG AGC GAT GAA CTA GAA ACG TTG TTC TTA TAC CGC GCG 1798
 135 Lys Gly Tyr Thr Gly Gly Gly Ser Asp Glu Leu Glu Thr Leu Phe Leu Tyr Arg Ala 154
         (t)                                                                  (j)

1799 GGT TAT TAC GCC GAG TTT TAC AAT GAC AAC ATC TCA TTT ATT GAA TGG GTC ACC CCA GCG 1858
 155 Gly Tyr Tyr Ala Glu Phe Tyr Asn Asp Asn Ile Ser Phe Ile Glu Trp Val Thr Pro Ala 174
                                              (l)

1859 GTG AAA GAA TCA GTG GAT GCG TTT GTT AAC ACA GCA AGC TTC TAC GAG AAC AGC CGT 1918
 175 Val Lys Glu Ser Val Asp Ala Phe Val Asn Thr Ala Ser Phe Tyr Glu Asn Ser Arg 194
         (e)                        (n)
```

FIG. 2D

```
1919 CAC GGC AAA GTG CTT AGT GAG GTC ATC ACT ATG GAT AGT GCG GGC TTG CAG CAC GCG 1978
 195 His Gly Lys Val Leu Ser Glu Val Ile Thr Met Asp Ser Ala Gly Leu Gln His Ala  214

1979 TAC TTA CCG CAA GTG ACC CAG TGG CTT ACT CGT TGG AAT GAT CAA TAC GCC CAG CAC TGG 2038
 215 Tyr Leu Pro Gln Val Thr Gln Trp Leu Thr Arg Trp Asn Asp Gln Tyr Ala Gln His Trp  234
                                                       (s)

2039 TAT ATG CGC AAT GCG GTT AAC GGT GTT TTC ACT ATT TTG TTT GGT GGG CAG TGG AAC GAG 2098
 235 Tyr Met Arg Asn Ala Val Asn Gly Val Phe Thr Ile Leu Phe Gly Gly Gln Trp Asn Glu  254

2099 CAA TTT GTG CAA ATA ATT GGC AAC CAA ACG GAC CTT GCC AAA GCT TTA GGC GAT TTT GCT 2158
 255 Gln Phe Val Gln Ile Ile Gly Asn Gln Thr Asp Leu Ala Lys Ala Leu Gly Asp Phe Ala  274
                                                                        (h)

2159 CTA AGG GCG TCA TCA ATC GGT GCT GAA GAT GAG TTT ATG GCC GCG AAT GCG GGG CGA GAG 2218
 275 Leu Arg Ala Ser Ser Ile Gly Ala Glu Asp Glu Phe Met Ala Asn Ala Gly Arg Glu  294
         (d)

2219 CTC GGG CGT CTG ACC AAG TAT ACG GGT AAC GCG AGT TCT GTT GTG AAG AGT CAG CTG AGT 2278
 295 Leu Gly Arg Leu Thr Lys Tyr Thr Gly Asn Ala Ser Ser Val Val Lys Ser Gln Leu Ser  314
                             (c)                                          (a)

2279 CGA ATC TTT GAA CAG TAT GAA ATG TAT GGT CGG GAC GCG GGT TGG CTT GCG GCG GCG 2338
 315 Arg Ile Phe Glu Gln Tyr Glu Met Tyr Gly Arg Asp Ala Val Trp Leu Ala Ala Ala  334

2339 GAC ACC GCC TCA TAT TAC GCA GAT TGT AGT GAG TTC GGA ATT TGT AAT TTC GAA ACT GAG 2398
 335 Asp Thr Ala Ser Tyr Tyr Ala Asp Cys Ser Glu Phe Gly Ile Cys Asn Phe Glu Thr Glu  354
         (r)
```

FIG. 2E

```
2399  CTA AAA GGC TTG GTG CTA TCG CAA ACT TAT ACT TGT AGC CCG ACA ATC CGA ATT TTG TCT  2458
 355  Leu Lys Gly Leu Val Leu Ser Gln Thr Tyr Thr Cys Ser Pro Thr Ile Arg Ile Leu Ser   374

2459  CAG AAT ATG ACG CAA GAG CAA CAC GCG GCC GCA TGT TCT AAA ATG GGT TAC GAA GAG GGT  2518
 375  Gln Asn Met Thr Gln Glu Gln His Ala Ala Ala Cys Ser Lys Met Gly Tyr Glu Glu Gly   394
                                                                     (g)

2519  TAC TTT CAT CAG TCA TTA GAA ACT GGT GAA CAG CCA GTA AAA GAT GAC CAC AAT ACT CAG  2578
 395  Tyr Phe His Gln Ser Leu Glu Thr Gly Glu Gln Pro Val Lys Asp Asp His Asn Thr Gln   414

2579  CTC CAA GTC AAT ATA TTC GAT TCA AGT ACC GAT TAT GGT AAG TAC GCA GGG CCA ATT TTC  2638
 415  Leu Gln Val Asn Ile Phe Asp Ser Ser Thr Asp Tyr Gly Lys Tyr Ala Gly Pro Ile Phe   434
                                       (o)

2639  GAT ATT AGT ACT GAC AAT GGC GGT ATG TAC TTG GAG GGC GAC CCT TCC CAG CCG GGG AAT  2698
 435  Asp Ile Ser Thr Asp Asn Gly Gly Met Tyr Leu Glu Gly Asp Pro Ser Gln Pro Gly Asn   454
      _____
                                                        (p)

2699  ATT CCC AAC TTT ATT GCT TAT GAA GCC TCT TAT GCG AAC GCA GAT CAC TTT GTC TGG AAC  2758
 455  Ile Pro Asn Phe Ile Ala Tyr Glu Ala Ser Tyr Ala Asn Ala Asp His Phe Val Trp Asn   474
      _____
                  (q)

2759  TTA GAG CAC GAA TAC GTG CAT TAC TTA GAT GGT CGA TTT GAT CTC TAT GGA GGG TTT AGT  2818
 475  Leu Glu His Glu Tyr Val His Tyr Leu Asp Gly Arg Phe Asp Leu Tyr Gly Gly Phe Ser   494
              _____
                                                 (m)

2819  CAT CCA ACT GAA AAA ATA GTG TGG AGT GAA GGC ATT GCA GAG TAT GTC GCT CAA GAA      2878
 495  His Pro Thr Glu Lys Ile Val Trp Trp Ser Glu Gly Ile Ala Glu Tyr Val Ala Gln Glu   514
      _____
                  (k)
```

FIG. 2F

| | | | | | | | | | | |
|---|---|---|---|---|---|---|---|---|---|---|
| 2879 | AAT | GAC | AAC | CAA | GCA | CTT | GAG | ACG | ATT | CTA | GAC | GGT | TCG | ACA | TAT | ACC | TTA | AGT | GAG | 2938 |
| 515 | Asn | Asp | Asn | Gln | Ala | Leu | Glu | Thr | Ile | Leu | Asp | Gly | Ser | Thr | Tyr | Thr | Leu | Ser | Glu | 534 |
| 2939 | ATT | TTC | GAG | ACT | ACT | TAT | GAT | GTC | GAT | GGG | TTT | GAT | GTC | GAT | CGA | ATT | TAT | CGT | TGG | GGG | TAC | TTA | 2998 |
| 535 | Ile | Phe | Glu | Thr | Thr | Tyr | Asp | Val | Asp | Gly | Phe | Asp | Val | Asp | Arg | Ile | Tyr | Arg | Trp | Gly | Tyr | Leu | 554 |
| | | | | | | | | | | | | | | | | | (i) | | | | | |
| 2999 | GCT | GTA | CGT | TTT | ATG | TTT | GAA | AAT | CAT | AAA | GAT | GAC | GTA | AAC | CAA | ATG | CTG | GTG | GAA | ACA | 3058 |
| 555 | Ala | Val | Arg | Phe | Met | Phe | Glu | Asn | His | Lys | Asp | Asp | Val | Asn | Gln | Met | Leu | Val | Glu | Thr | 574 |
| | | (b) | | | | | | | | | | | | | | | | | | |
| 3059 | CGC | CAA | GGG | AAT | TGG | ATC | AAT | TAC | AAG | GCC | ACG | ATC | ACC | CAA | TGG | GCG | AAT | TTG | TAT | CAA | 3118 |
| 575 | Arg | Gln | Gly | Asn | Trp | Ile | Asn | Tyr | Lys | Ala | Thr | Ile | Thr | Gln | Trp | Ala | Asn | Leu | Tyr | Gln | 594 |
| | (f) | | | | | | | | | | | | | | | | | | | |
| 3119 | AGT | GAG | TTT | GAG | CAG | TGG | CAG | CAA | ACC | CTT | GTC | TCA | AAT | GGT | GCT | CCT | AAT | GCA | GTC | ATA | 3178 |
| 595 | Ser | Glu | Phe | Glu | Gln | Trp | Gln | Gln | Thr | Leu | Val | Ser | Asn | Gly | Ala | Pro | Asn | Ala | Val | Ile | 614 |
| 3179 | ACC | GCA | AAC | AGT | AAG | GGG | AAA | GTC | GGT | GAA | AGC | ATT | ACA | TTT | AGC | AGT | GAA | AAC | AGT | ACA | 3238 |
| 615 | Thr | Ala | Asn | Ser | Lys | Gly | Lys | Val | Gly | Glu | Ser | Ile | Thr | Phe | Ser | Ser | Glu | Asn | Ser | Thr | 634 |
| 3239 | GAC | CCA | AAC | GGG | AAG | ATC | GTC | TTA | TGG | GAC | TTC | GGT | GAT | GGC | TCG | ACA | AGT | ACA | 3298 |
| 635 | Asp | Pro | Asn | Gly | Lys | Ile | Val | Leu | Trp | Asp | Phe | Gly | Asp | Gly | Ser | Thr | Ser | Thr | 654 |
| 3299 | CAA | ACC | AAG | CCG | ACG | CAC | CAA | TAT | GGG | GAG | TAT | TCG | GTC | AGC | CTA | AGT | GTG | 3358 |
| 655 | Gln | Thr | Lys | Pro | Thr | His | Gln | Tyr | Gly | Glu | Tyr | Ser | Val | Ser | Leu | Ser | Val | 674 |

FIG. 2G

```
3359  ACA GAC AGT GAA GGC TTG ACG GCA ACC GCC ACT CAT ACT GTT ATC TCA GCG TTG GGC  3418
675   Thr Asp Ser Glu Gly Leu Thr Ala Thr Ala Thr His Thr Val Ile Ser Ala Leu Gly  694

3419  GGT AAT GAC ACA TTG CCA CAA GAC TGC GCG GTG CAA AGT AAA GTA AGC GGT GGG CGC TTA  3478
695   Gly Asn Asp Thr Leu Pro Gln Asp Cys Ala Val Gln Ser Lys Val Ser Gly Gly Arg Leu  714

3479  ACA GCA GGA GAA CCA GTT TGC TTG GCA AAT CAA CAA ACC ATT TGG CTG AGC GTA CCA GCG  3538
715   Thr Ala Gly Glu Pro Val Cys Leu Ala Asn Gln Gln Thr Ile Trp Leu Ser Val Pro Ala  734

3539  GTG AAT GAG AGC TCA AAC CTG GCG ATA ACG ACG GGG AAT GGT ACG GGC AAC CTA AAG CTT  3598
735   Val Asn Glu Ser Ser Asn Leu Ala Ile Thr Thr Gly Asn Gly Thr Gly Asn Leu Lys Leu  754

3599  GAA TAC AGT AAC TCT GGT TGG CCG GAT GAT ACT AAT CTT CAC GGG TGG TCA GAT AAT ATT  3658
755   Glu Tyr Ser Asn Ser Gly Trp Pro Asp Asp Thr Asn Leu His Gly Trp Ser Asp Asn Ile  774

3659  GGT AAT GGA GAG TGT ATT ACG TTG TCA AAT CAG AGT AAC TAC TGG GGC TAC GTT AAA GTC  3718
775   Gly Asn Gly Glu Cys Ile Thr Leu Ser Asn Gln Ser Asn Tyr Trp Gly Tyr Val Lys Val  794

3719  TCT GGT GAC TTT GAG AAT GCC ATC GTC GTT GAT GCT CAG AAG TGT CGT CAG  3778
795   Ser Gly Asp Phe Glu Asn Ala Ile Val Val Asp Ala Gln Lys Cys Arg Gln  814

3779  TAG GGC AAT TTA ACT ACG TCA TTT AAA CTA AGT GGA GCG CCT CGC TAA CAT CGC GGG GGC  3838
3839  TTT TTG TTT TTA CGC CGT TAT CTC TAT AAA AAA AAC CAG CCC GAA GGC TGG CAA ACA AGA  3898
```

FIG. 2H

```
3899  AGT TTG AGA TGA AAA TGA AAA CGT TAT AAA ACT TGC TGA TAT CCT ATT TCT CAA TAA GTT  3958
3959  GGG TTG TGC TTT GCA GCC AGT TTT TAT CTT GCG CAT CAA GAA AAA GGG CTA AGC GCC TGA  4018
4019  TAG ACA CGT GAA TGG TAA TGA TTA AGC CAG TCT CGC                                   4054
```

1. JM109
2. JM109(pLC0-1)
3. JM109(pHUC14)

BACTERIAL COLLAGENASE GENE OF
*VIBRIO ALGINOLYTICUS +l*

FIELD OF THE INVENTION

The present invention relates to a collagenase gene derived from *Vibrio alginolytic*, a recombinant vector integrating the gene, a host cell transformed with the vector, and the use thereof.

BACKGROUND OF THE INVENTION

Collagen which constitutes connective tissues of animals is composed of three polypeptide chains, each basic unit of which has a molecular weight of about 95,000. These polypeptide chains form a counterclockwise triplex spiral structure. The amino acid sequence of each polypeptide chain of the collagen molecule is a repetition of Gly-Pro-X-Gly (wherein the three-letter code representing amino acid residues SEQ ID No: 1) used herein are those according to IUPAC-IUB standards and X represents various amino acid residues) and the polypeptides are intramolecularly or intermolecularly cross-linked. This specific spiral structure of collagen brings about tough mechanical properties and chemical stability and, therefore, collagen resists degradation by ordinary proteases and only a collagenase can degrade collagen.

A collagenase does not act on ordinary proteins, but acts on only the above collagen or its modified product, gelatin. Collagenases are produced by microorganisms and, among these collagenases, the study on the collagenase known as Achromobacter collagenase which is derived from *Vibrio alginolyticus chemovar. iophagus* is most advanced. It has been known that this collagenase has a higher specific activity in comparison with collagenases derived from other sources [V. Keil-Dlouha and B. Keil, Biochim. Biophys. Acta, 522, 218–228 (1978)]. Achromobacter collagenase has a molecular weight of 110,000 and is stable at pH 6 to 7. The optimum pH is about pH 7.4. The collagenase, which is inactivated by EDTA and o-phenanthroline [V. Keil-Dlouha, Biochim. Biophys. Acta, 429, 239–251 (1976)], is a metalloprotease containing zinc, and breaks the synthetic substrate, PZ-Pro-Leu-Gly-Pro-D-Arg, between Leu and Gly [B. Keil, A. M. Gilles, A. Lecroisey, N. Hurion and N. T. tong, FEBS Lett., 56, 292–296 (1975); A. Lecroisey, V. Keil-Dlouha, D. R. Woods, D. Perrin and B. Keil, FEBS Lett., 59, 167–172 (1975); N. T. Tong, A. Tsugita and V. Keil-Dlouha, Biochim. Biophys. Acta, 874, 296–304 (1986)].

In view of the specific property of a collagenase, various uses have been expected and realized. For example, a collagenase is used for treatment of various injuries of any substrate having a structure rich in collagen. Examples of such injuries include burn, ulcer, scab, white hard scab of collagen base, cheloid, necrosis, particularly, necrosis by decubitus or ulcer, and the like.

A collagenase is also used for treatment of dental caries. Namely, the dental pulp is mainly composed of a dense calcareous material and collagen. In the case of dental caries, a tooth is cracked or a hole is made and calcium is leaked therefrom. Accordingly, the calcareous material is lost, and the remaining frame becomes porous and is liable to be a hotbed of bacterial infection. However, since a collagenase dissolves the porous collagen, the hotbed can be removed by washing with water. A collagenase does not act on healthy calcareous collagen.

In addition, a collagenase can be used as an agent for making meat tender. Toughness of meat is mainly caused by tendon, the main component of which is collagen. Proteases such as papain and the like are used to make meat tender by degrading tendon. However, collagen is hardly degraded by ordinary proteases. On the other hand, non-specific proteases such as papain also degrade proteins such as actin, myosin and the like which have great influence on the texture 0f meat. Therefore, the texture of meat is destroyed by treatment with papain. In this respect, since a collagenase degrades only collagen which causes toughness of meat, but does not degrade other proteins which have great influence on the texture of meat, the enzyme is a protease most suitable for an agent for making meat tender.

In the use of a collagenase for the above purposes, there is a problem that it is very difficult to obtain a collagenase at a low cost. Namely, in order to obtain Achromobacter collagenase, its producer, *Vibrio alginolyticus*, is cultivated and the collagenase is recovered from the culture solution and purified. However, in this respect, there is a problem that the yield of collagenase by the producer is very low such as 10 mg/liter. Further, there is another problem that any collagenase is not produced by the producer unless a certain specific inducing substance is added to a culture medium. Thus, it is very difficult to obtain the collagenase in a large amount at a low cost.

Although it is possible to employ genetic engineering techniques to solve these problems, no gene of Achromobacter collagenase is yet available. Therefore, no genetic engineering technique can be employed to produce the enzyme in a large amount.

OBJECTS OF THE INVENTION

The present inventors have studied intensively to solve these problems. As a result, the present inventors have successfully obtained a gene of Achromobacter collagenase and clarified its amino acid sequence, whereby it is possible to produce Achromobacter collagenase in a large amount in a suitable host and to improve the availability of a collagenase by means of genetic engineering techniques.

One object of the present invention is to provide a gene encoding Achromobacter collagenase.

Another object of the present invention is to provide a recombinant vector containing the gene of Achromobacter collagenase.

Still another object of the present invention is to provide a host cell transformed by the vector.

Still another object of the present invention is to provide a process for the production of Achromobacter collagenase by using the host cell.

These objects as well as other objects and advantages of the present invention will become apparent to those skilled in the art from the following description with reference to the accompanying drawings.

BRIEF EXPLANATION OF DRAWINGS

In FIG. 1, the arrow at the bottom part represents the collagenase structural gene region as well as the direction of transcription. The number in the parentheses is that of the base. The dotted line means that the restriction cleavage site can not be specified between the two sites.

FIG. 2 is the entire DNA base sequence of a DNA fragment containing the collagenase gene and an amino acid sequence of the collagenase deduced from the base sequence (SEQ ID No: 2). In FIG. 2, the regions underlined by the solid line represent the parts corresponding to the partial amino acid sequences (see Example 3 hereinafter) of the purified collagenase.

In FIG. 3, the arrows represent the migration positions of markers having various molecular weights which were subjected to Western blotting simultaneously.

SUMMARY OF THE INVENTION

Figure 1:
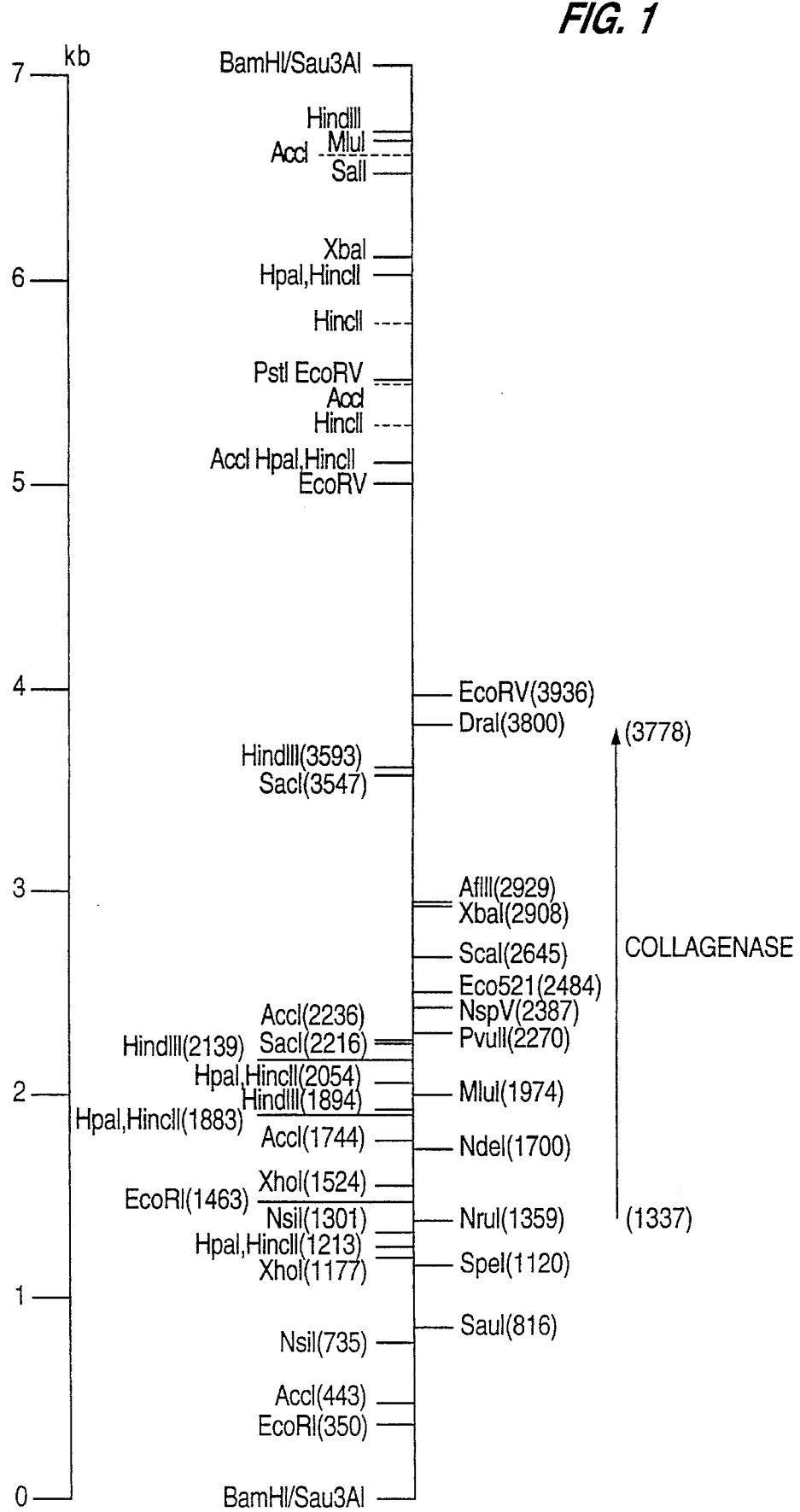
FIG. 1 is a restriction map of a DNA fragment of 7.0 kb containing the collagenase gene of the present invention which composes the plasmid pLCO-1.

According to the present invention, there is provided a collagenase gene derived from bacteria of the species *Vibrio alginolyticus*.

The present invention also provides a recombinant vector containing the above gene of the present invention or a biologically equivalent thereof, and a host cell transformed with a plasmid containing the gene of the present invention.

The present invention further provides a process for the production of a collagenase which comprises cultivating the host cells to produce the collagenase and recovering the collagenase thus produced from the cells or culture solution.

DETAILED DESCRIPTION OF THE INVENTION

The bacteria of the species *Vibrio alginolyticus* to be used for obtaining the collagenase gene of the present invention is not specifically limited and any known producer of Achromobacter collagenase can be used. For example, *Vibrio alginolyticus* disclosed by I. Emonto et al. in Int. J. Syst. Bacteriol., 33,451–459, 1983. Further, the isolation of a bacterial DNA, preparation of a gene library and screening can be conducted according to the conventional methods as shown in Examples hereinafter.

As host cells, *Escherichia coli*, *Bacillus subtilis* and the like can be used. As vectors, pUC18, pUC19, pBR322, pGEM3, pGEM4 and the like which can be replicated in *Escherichia coli* as well as pUB110, pE194, pC194 and the like which can be replicated in *Bacillus subtilis* can be used.

In order to produce a collagenase by using the host cells transformed by the plasmid containing the collagenase gene thus obtained, for example, the cells are cultivated in a suitable culture medium containing suitable carbon sources, nitrogen sources and trace amounts of metallic elements according to the method described by A. Lecroisey et al. in FEBS Lett., 59,167–172, 1975. The resultant culture is recovered by the conventional method and the supernatant of the culture is subjected to ammonium sulfate precipitation (60% saturated). Then, the enzyme is purified by chromatography, for example, DEAE column chromatography, Sephadex G-100 column chromatography and the like to obtain the desired collagenase.

The collagenase thus obtained can be used according to the same manner as that of known collagenases.

The following Examples further illustrate the present invention in detail but are not to be construed to limit the scope thereof.

Example 1

Preparation of gene library

According to the conventional method [e.g., Saito-Miura Method (H. Saito and K. Miura, Biochem. Biophys. Acta, 72, 619, 1963), etc.], chromosomal DNA was isolated from an Achromobacter collagenase producer, *Vibrio alginolyticus* obtained from The National Collection of Industrial Bacteria (NCIB) [VIBRIO ALGINOLYTICUS SUBSP, IOPHAGUS AL, 11038 R. L. Welton/South African cured hides/(62SC)]. The DNA was partially cleaved with the restriction enzyme Sau3A1 and fractionated by agarose gel electrophoresis to obtain a DNA fragment of 5 kb or more. The DNA fragment was ligated to the vector pUC18 treated with BamHI by T4 ligase. *Escherichia coli* JM101 was transformed by the resultant ligation mixture according to the conventional method (e.g., M. Mandel and A. Higa, J. Mol. Biol., 53, 154, 1970) to obtain a gene library of *Vibrio alginolyticus* as an ampicillin resistant transformant.

Example 2

Screening of gene library

In order to select a transformant producing the collagenase, Achromobacter collagenase antibody was prepared according to the conventional method [e.g., Zoku-Seikagaku Zikken Ho (Methods of Biochemical Experiments Second Series), edited by the Biochemical Society of Japan, Vol. 5, pp. 1 to 25, 1986]. Namely, a purified collagenase (1 mg) was mixed with Freund's incomplete adjuvant and a rabbit was immunized by subcutaneously injecting the mixture. Further, the same operation was repeated once a week for 3 weeks to give booster immunization. In the fourth week, whole blood was collected and an IgG fraction was prepared by ammonium sulfate fractionation. The antibody was labeled with peroxidase according to a known method such as that using sodium periodate [Meneki Zikkensosa Ho (Methods for Immunological Experiments) VI, edited by the Immunological Society of Japan, p 1835].

The anti-collagenase antibody labeled with the enzyme thus Obtained was used for selection of clones expressing an antigen which was able to react with the antibody from the above-prepared gene library to obtain plasmids pLCO-1, pLCO-2 and pLCO-3.

The plasmid pLCO-1 has a DNA fragment of about 7.0 kb derived from *Vibrio alginolyticus* inserted therein. The restriction map of the DNA fragment inserted in pLCO-1 is shown in FIG. 1.

Further, *Escherichia coli* JM101 containing the plasmid pLCO-1 was named as *Escherichia coli* SAM 1514 and deposited with Fermentation Research Institute, Agency of Industrial Science and Technology (FRI) under Budapest treaty on Nov. 22, 1989 under the accession number of FERM BP-3113.

Example 3

Determination of amino acid sequence

Partial amino acid sequences of Achromobacter collagenase were determined as follows:

Purified Achromobacter collagenase was partially hydrolyzed with trypsin or protease V8, respectively according to the conventional method (e.g., Zoku-Seikagaku Zikken Ho, Vol. 2, pp. 260–270, edited by the Biochemical Society of Japan). The peptide fragments thus obtained were purified by high performance liquid chromatography and then their amino acid sequences were determined by automatic Edman degradation method.

As a result, it has been found that Achromobacter collagenase of the present invention has the amino acid sequences of the following 20 peptide fragments.

(a): S Q L S R
(b): I Y R
(c): Y T G N A S S V V K (d): A S S I G A E D E F M A A N A G R E
(e): E S V D A F V N
(f): Q G N W I N Y K
(g): M G Y E E G Y F H Q S L
(h): A L G D F A L R
(i): W G Y L A V R
(j): A G Y Y A E
(k): V W W S E
(l): W V T P A V K E
(m): L D G R F D L Y G G F S H P T E K
(n): Y N D N I S F
(o): S S T D Y G K Y A G P I F D
(p): G D P S Q P G N I P N F I A Y E
(q): Y V H Y L D G R F D
(r): T A S Y Y A D C S E
(s): W N D Q Y
(t): G Y T G G G S D E L wherein A is alanine, C is cysteine, D is aspartic acid, E is glutamic acid, F is phenylalanine, G is glycine, H is histidine, I is isoleucine, K is lysine, L is leucine, M is methionine, N is asparagine, P is proline, Q is glutamine, R is arginine, S is serine, T is threonine, V is valine, W is tryptophan and Y is tyrosine.

Example 4

Determination of DNA base sequence

The base sequence of the fragment of 4.1 kb in the DNA fragment of 7.0 kb composing the plasmid pLCO-1 was determined as follows:

Namely, the plasmid pLCO-1 was cleaved with various restriction enzymes to prepare DNA fragments of about 500 bp. These fragments were cloned into phage M13 and the DNA base sequences of each recombinant phage DNA were determined by dideoxy method (F. Sanger et al., Proc. Nat. Acad. Sci. USA, 74, 5963–5967, 1977). A DNA base sequence of about 4 kb was determined by joining respective sequences of DNA fragments.

The DNA base sequence thus determined is shown in FIG. 2. The DNA base sequence is composed of 4054 base pairs and the entire region of Achromobacter collagenase gene is contained therein. As seen from FIG. 2, there is an open reading frame corresponding to the collagenase which is composed of 2442 base pairs initiated from ATG of Base Nos. 1337 to 1339 and terminated by TAG of Base Nos. 3779 to 3781 in the DNA sequence. The ribosome binding site, GAAGAAA, is located at 5 bp prior to the ATG initiation codon.

When amino acid sequences deduced from the DNA base sequence thus determined were compared with the partial amino acid sequences determined in Example 3, the following 20 amino acid sequences agreed with each other.

(a)SQLSR (SEQ ID NO: 3)
AGTCAGCTCAGTCGA
SerGlnLeuSerArg (b)IYR
ATTTATCGT
IleTyrArg (c)YTGNASSVVK (SEQ ID NO: 4)
TATACGGGTAACGCGAGTTCTGTTGTGAAG
TyrThrGlyAsnAlaSerSerValValLys (d)ASSIGAEDEFMAANAGRE (SEQ ID NO: 5)
GCGTCATCAATCGGTGCTGAAGATGAGTTTATGGCCGCCAATGCGGGGCGAGAG
AlaSerSerThrGlyAlaGluAspGluPheMetAlaAlaAsnAlaGlyArgGlu (e)ESVDAFVN (SEQ ID NO: 6)
GAATCAGTGGATGCGTTTGTTAAC
GluSerValAspAlaPheValAsn (f)QGNWINYK (SEQ ID NO: 7)
CAAGGGAATTGGATCAATTACAAG
GlnGlyAsnTrpIleAsnTyrLys (g)MGYEEGYFHQSL (SEQ ID NO: 8)
ATGGGTTACGAAGAGGGTTACTTTCATCAGTCATTA
MetGlyTyrGluGluGlyTyrPheHisGlnSerLeu (h)ALGDFALR (SEQ ID NO: 9)
GCTTTAGGCGATTTTGCTCTAAGG
AlaLeuGlyAspPheAlaLeuArg (i)WGYLAVR (SEQ ID NO: 10)
TGGGGGTACTTAGCTGTACGT
TrpGlyTyrLeuAlaValArg (j)AGYYAE (SEQ ID NO: 11)
GCGGGTTATTACGCCGAG
AlaGlyTyrTyrAlaGlu (k)VWWSE (SEQ ID NO: 12)

-continued

GTGTGGTGGAGTGAA
ValTrpTrpSerGlu (l)WVTPAVKE (SEQ ID NO: 13)
TGGGTCACCCCAGCCGTGAAAGAA
TrpValThrProAlaValLysGlu (m)LDGRFDLYGGFSHPTEK (SEQ ID NO: 14)
TTAGATGGTCGATTTGATCTCTATGGAGGGTTTAGTCATCCAACTGAAAAA
LeuAspGlyArgPheGluLeuTyrGlyGlyPheSerHisProThrGluLys (n)YNDNISF (SEQ ID NO: 15)
TACAATGACAACATCTCATTT
TyrAsnGluAsnIleSerPhe (o)SSTDYGKYAGPIFD (SEQ ID NO: 16)
TCAAGTACCGATTATGGTAAGTACGCAGGGCCAATTTTCGAT
SerSerThrGluTyrGlyLysTyrAlaGlyProIlePheGlu (p)GDPSQPGNIPNFIAYE (SEQ ID NO: 16)
GGCGACCCTTCCCAGCCGGGGAATATTCCCAACTTTATTGCTTATGAA
GlyAspProSerGlnProGlyAsnIleProAsnPheIleAlaTyrGlu (q)YVHYLDGRFD (SEQ ID NO: 18)
TACGTGCATTACTTAGATGGTCGATTTGAT
TyrValHisTyrLeuAspGlyArgPheAsp (r)TASYYADCSE (SEQ ID NO: 19)
ACCGCCTCATATTACGCAGATTGTAGTGAG
ThrAlaSerTyrTyrAlaAspCysSerGlu (s)WNDQY (SEQ ID NO: 20)
TGGAATGATCAATAC
TrpAsnAspGlnTyr (t)GYTGGGSDEL (SEQ ID NO: 21)
GGGTATACGGGTGGCGGGAGCGATGAACTA
GlyTyrThrGlyGlyGlySerAspGluLeu

Example 5

Analysis of gene product

A recombinant plasmid for the mass production of the collagenase gene in *Escherichia coli* was prepared.

BamHI linker was inserted into HpaI site at Base No. 1213 on the DNA fragment of 7 kb composing the plasmid pLCO-1 and SalI linker was inserted into EcoRV site at Base NO. 3936 on the DNA fragment. The resultant pLCO-1 containing these two linkers was cleaved with BamHI and SalI to obtain a DNA fragment of 2.7 kb containing the entire collagenase gene. The DNA fragment was recovered and inserted into BamHI/SalI site of the vector pUC18 to obtain a recombinant plasmid pHUC14. *Escherichia coli* JM109 was transformed with the recombinant plasmid pHUC14 to obtained a recombinant *Escherichia coli* for the mass production of the collagenase.

The Achromobacter collagenase gene product in the recombinant *Escherichia coli* was analyzed by electrophoresis and Western blotting. Western blotting was conducted by modified Burnette method [Burnette, W. N., Anal. Biochem., 112,680–685 (1981)].

Figure 3:
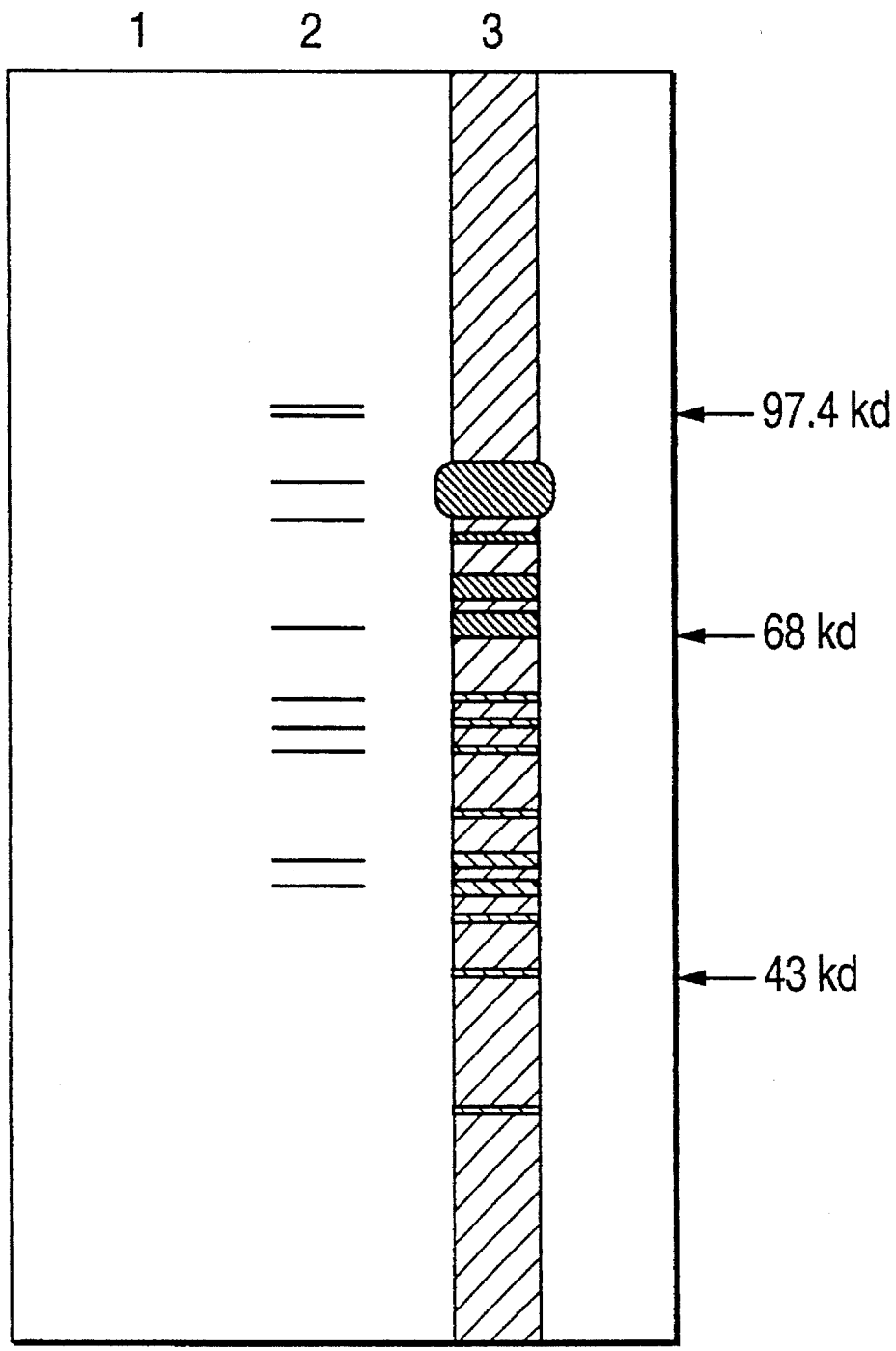
FIG. 3 illustrates an analytical result of Western blotting of a collagenase gene product in *Escherichia coli*.

The recombinant *Escherichia coli* containing the collagenase gene was cultured in L-broth containing 1 mM of IPTG at 37° C. for 17 hours. The cells were collected by centrifugation and broken by sonication. The sonicated cell suspension was fractionated by SDS-polyacrylamide gel electrophoresis. The protein thus fractionated was translated to a nitrocellulose membrane by Western blotting and color of only the bands of the collagenase was developed by an anti-collagenase antibody from a rabbit and an anti-rabbit IgG antibody labeled with peroxidase according to the same manner as that described above. As shown in FIG. 3, many bands which reacted with the anti-collagenase antibody mainly composed of protein having the molecular weight of about 85 kd were observed in *Escherichia coli* JM109 containing pHUC14. In *Escherichia coli* JM109 containing pLCO-1, protein which reacted with the anti-collagenase antibody was also observed, although the amount thereof was very small. On the other hand, in *Escherichia coli* JM109 containing no recombinant plasmid used as a control, no protein which reacted with the anti-collagenase antibody was observed.

These results show that protein which is an immunologically equivalent to Achromobacter collagenase is produced in *Escherichia coli* containing the recombinant plasmid pLCO-1 or pHUC14 and a large amount of the protein is produced by *Escherichia coli* containing the recombinant plasmid pHUC14.

Example 6

Collagenase activity of transformant

Collagenase activity of *Escherichia coli* containing Achromobacter collagenase gene was measured by using the synthetic substrate, 4-phenylazo-benzyloxycarbonyl-L-Pro-Leu-Gly-L-Pro-D-Arg.HCl (PZ-PLGPR).

The measurement of collagenase activity and the definition of the unit of the activity (U) are disclosed in International Publication WO 84/02653.

The sonicated cell solution was prepared according to the same manner as that disclosed in Example 5. As shown in Table 1, an coliagenase activity was observed in *Escherichia coli* JM109 containing the plasmid pHUC14. No activity was observed in *Escherichia coli* JM109 containing the plasmid pLCO-1 or containing no plasmid.

In view of these results, it is clear that the gene product in the recombinant *Escherichia coli* containing the collagenase gene has collagenase activity. Although no collagenase activity is observed in *Escherichia coli* containing the plasmid pLCO-1, this would be due to a low expression level.

TABLE 1

| Collagenase activity of recombinant *Escherichia coli* | |
|---|---|
| Plasmid | Collagenase activity |
| no | <5 |
| pLCO-1 | <5 |
| pUC14 | 189 |

Note) "Plasmid" means *Escherichia coli* JM109 containing the corresponding plasmid.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:

-continued

```
              ( D ) DEVELOPMENTAL STAGE:
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY:
              ( B ) LOCATION:
              ( C ) IDENTIFICATION METHOD:
              ( D ) OTHER INFORMATION:

( x ) PUBLICATION INFORMATION:
              ( A ) AUTHORS:
              ( B ) TITLE:
              ( C ) JOURNAL:
              ( D ) VOLUME:
              ( E ) ISSUE:
              ( F ) PAGES:
              ( G ) DATE:
              ( H ) DOCUMENT NUMBER:
              ( I ) FILING DATE:
              ( J ) PUBLICATION DATE:
              ( K ) RELEVANT RESIDUES IN SEQ ID NO:

( x i ) SEQUENCE DESCRIPTION: SEQ ID NO:1:

Gly   Pro   Xaa   Gly
                      1
```

( 2 ) INFORMATION FOR SEQ ID NO:2:

```
        ( i ) SEQUENCE CHARACTERISTICS:
              ( A ) LENGTH: 4054 base pairs
              ( B ) TYPE: nucleic acid
              ( C ) STRANDEDNESS: single
              ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
              ( A ) ORGANISM: Vibrio alginolyticus
              ( B ) STRAIN:
              ( C ) INDIVIDUAL ISOLATE:
              ( D ) DEVELOPMENTAL STAGE:
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY:
```

( B ) LOCATION:
( C ) IDENTIFICATION METHOD:
( D ) OTHER INFORMATION: /note="location 1337 to 3781 base pairs open reading frame"

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:2:

```
GATCGTACCA GTCATTATAT CTGCTGCTGC GATGTACTTT TTCTACACAC GCCTTGGCTT      60

ATCACAAACT TATCTAGGCG TCATTTTGGC ACACGCTGCG TTAGGTACGC CTTTTGTCGT     120

CATTACCGTT ACTGCGACGT TAAGTGGCTT TGACCATAGC TTGGTAAAAG CGGCGGCTAG     180

CTTAGGAGCA AACCCTGTTT ATACTTTCAG ACACATTACC TTTAAGCTGA TTCGTCCGGG     240

GATGATTTCT GGCGGCTTGT TTGCCTTTGA GCATCGTTCG ACGAGGTTGT GGTGGCGTTA     300

TTCCTGACTG GGGCAGAACA AAAAACCGTT CCGAGGCAGA TGTGGTCAGG AATTCGAGAG     360

CAAATTAGTC CGACCATATT GGCGGTCGCT ACGTTGTTGA TTTTTATGTC GGTGTGTTTG     420

CTCGTGACGT TAGAAGTTTT GCGTAGACGT AATATACGCA TTCGAGGCAT TCAAGAATAA     480

CCAGACTTTT TCTTTGTTGG TCACTATGCA CTTTTGTTTA GGGGCACCTC AATTTTTGAC     540

CAAAGGCGCC TTATTGTAGG CGCTTTTCTT TTGTGTTTGT CGTCAGCGAT GACTGACATG     600

TCACTCTTGT AGCTTAATGC CAGCCTGCTC GAAACGTGCC AAAGGCGACT TGTTCGATTG     660

CTGATACCAA CTAGCTGGCA TGTTTGGTTT AAGTCGGGCT TTTTCATCCT TGCTAATCAC     720

AACATAGTGT AAAAATGCAT CAAGTGTGGT TCCCATCACG TCAAACGTCA TTTCCCCACC     780

TTTGCTGATG GTTTTCAATA ATCCAACGAC GGCTTCCTCA GGGACTAACG GTTCAACCAC     840

CGCGTTTTTT CGCTCTTTTA TTGATGTTGA AGCGGGCAGG TTTGCACGTG CCGTCTCCCA     900

GCAAACTTTG TTGGTTTTAC TGACAAGGTT GTGCTTGTAG CAGTAGTAAC TGAATAAAAA     960

GCGTGGCAGA TTTTGCCAGC GTTCGGCTTG GACTTCTAAC CAAAGGTGTT GTAGCTCAAT    1020

ATCAGCGTCG GTCATAGGAG TTGTTTAGCA AAAAGAAAAG AAACCATTTT ATCGCTTTTG    1080

TGAGGAGCAA TAAAAGATAT TTGAATGGAA AGATAAACAA CTAGTTTATC AATATTACTA    1140

AAGCAAATAG ATTTCTGGCA AGCCCGTGCA ACGCAACTCG AGTACCAAAA ACTGATACCG    1200

CCACATTCGG TTGTTAACAA AATGTTTCTT CTTGTCTTGC GAGTAGATTA TATGGAGATG    1260

CTCTTGCAGT AATAAGGGCA GTGGCGATGC AAAAGACGTA ATGCATCTAA GGAAAACTCA    1320

ATATAGAAGA AATTAG ATG GAA CTG AAG ATT TTG AGT GTC GCG ATT GCG ACA    1372
                Met Glu Leu Lys Ile Leu Ser Val Ala Ile Ala Thr
                  1               5                  10

ACA TTA ACC AGC ACT GGC GTA TTT GCG TTA AGC GAG CCA GTT TCT CAA       1420
Thr Leu Thr Ser Thr Gly Val Phe Ala Leu Ser Glu Pro Val Ser Gln
         15                  20                  25

GTT ACA GAG CAA CAT GCA CAT TCG GCT CAT ACA CAC GGT GTT GAA TTC       1468
Val Thr Glu Gln His Ala His Ser Ala His Thr His Gly Val Glu Phe
     30                  35                  40

AAT CGA GTT GAA TAC CAA CCA ACC GCA ACT CTC CCA ATT CAG CCC TCT       1516
Asn Arg Val Glu Tyr Gln Pro Thr Ala Thr Leu Pro Ile Gln Pro Ser
 45                  50                  55                  60
```

| | | | | | | | | | | | | | | | | |
|---|---|---|---|---|---|---|---|---|---|---|---|---|---|---|---|---|
| AAG | GCA | ACT | CGA | GTA | CAG | TCA | CTT | GAA | AGC | CTT | GAT | GAG | TCG | AGC | ACT | 1564 |
| Lys | Ala | Thr | Arg | Val 65 | Gln | Ser | Leu | Glu | Ser 70 | Leu | Asp | Glu | Ser | Ser 75 | Thr | |
| GCT | TGT | GAT | TTG | GAG | GCA | TTG | GTT | ACC | GAA | AGC | AGT | AAC | CAA | TTG | ATC | 1612 |
| Ala | Cys | Asp | Leu 80 | Glu | Ala | Leu | Val | Thr 85 | Glu | Ser | Ser | Asn | Gln 90 | Leu | Ile | |
| AGC | GAA | ATT | TTA | AGT | CAG | GGC | GCG | ACG | TGT | GTG | AAC | CAG | TTA | TTC | TCT | 1660 |
| Ser | Glu | Ile 95 | Leu | Ser | Gln | Gly | Ala 100 | Thr | Cys | Val | Asn | Gln 105 | Leu | Phe | Ser | |
| GCT | GAA | AGT | CGG | ATT | CAA | GAG | TCG | GTA | TTT | AGC | TCC | GAT | CAT | ATG | TAC | 1708 |
| Ala | Glu | Ser 110 | Arg | Ile | Gln | Glu | Ser 115 | Val | Phe | Ser | Ser | Asp 120 | His | Met | Tyr | |
| AAC | ATC | GCT | AAG | CAC | ACT | ACG | ACG | TTG | GCG | AAG | GGG | TAT | ACG | GGT | GGC | 1756 |
| Asn 125 | Ile | Ala | Lys | His | Thr 130 | Thr | Thr | Leu | Ala | Lys 135 | Gly | Tyr | Thr | Gly | Gly 140 | |
| GGG | AGC | GAT | GAA | CTA | GAA | ACG | TTG | TTC | TTA | TAC | TTA | CGC | GCG | GGT | TAT | 1804 |
| Gly | Ser | Asp | Glu | Leu 145 | Glu | Thr | Leu | Phe | Leu 150 | Tyr | Leu | Arg | Ala | Gly 155 | Tyr | |
| TAC | GCC | GAG | TTT | TAC | AAT | GAC | AAC | ATC | TCA | TTT | ATT | GAA | TGG | GTC | ACC | 1852 |
| Tyr | Ala | Glu | Phe 160 | Tyr | Asn | Asp | Asn | Ile 165 | Ser | Phe | Ile | Glu | Trp 170 | Val | Thr | |
| CCA | GCG | GTG | AAA | GAA | TCA | GTG | GAT | GCG | TTT | GTT | AAC | ACA | GCA | AGC | TTC | 1900 |
| Pro | Ala | Val 175 | Lys | Glu | Ser | Val | Asp 180 | Ala | Phe | Val | Asn | Thr 185 | Ala | Ser | Phe | |
| TAC | GAG | AAC | AGC | GAC | CGT | CAC | GGC | AAA | GTG | CTT | AGT | GAG | GTC | ATC | ATC | 1948 |
| Tyr | Glu | Asn 190 | Ser | Asp | Arg | His | Gly 195 | Lys | Val | Leu | Ser | Glu 200 | Val | Ile | Ile | |
| ACT | ATG | GAT | AGT | GCG | GGC | TTG | CAG | CAC | GCG | TAC | TTA | CCG | CAA | GTG | ACC | 1996 |
| Thr | Met | Asp | Ser | Ala | Gly | Leu | Gln | His | Ala | Tyr | Leu | Pro | Gln | Val | Thr | |
| 205 | | | | 210 | | | | | 215 | | | | | | 220 | |
| CAG | TGG | CTT | ACT | CGT | TGG | AAT | GAT | CAA | TAC | GCC | CAG | CAC | TGG | TAT | ATG | 2044 |
| Gln | Trp | Leu | Thr | Arg 225 | Trp | Asn | Asp | Gln | Tyr 230 | Ala | Gln | His | Trp | Tyr 235 | Met | |
| CGC | AAT | GCG | GTT | AAC | GGT | GTT | TTC | ACT | ATT | TTG | TTT | GGT | GGG | CAG | TGG | 2092 |
| Arg | Asn | Ala | Val | Asn 240 | Gly | Val | Phe | Thr | Ile 245 | Leu | Phe | Gly | Gly | Gln 250 | Trp | |
| AAC | GAG | CAA | TTT | GTG | CAA | ATA | ATT | GGC | AAC | CAA | ACG | GAC | CTT | GCC | AAA | 2140 |
| Asn | Glu | Gln 255 | Phe | Val | Gln | Ile | Ile 260 | Gly | Asn | Gln | Thr | Asp 265 | Leu | Ala | Lys | |
| GCT | TTA | GGC | GAT | TTT | GCT | CTA | AGG | GCG | TCA | TCA | ATC | GGT | GCT | GAA | GAT | 2188 |
| Ala | Leu | Gly 270 | Asp | Phe | Ala | Leu | Arg 275 | Ala | Ser | Ser | Ile | Gly 280 | Ala | Glu | Asp | |
| GAG | TTT | ATG | GCC | GCG | AAT | GCG | GGG | CGA | GAG | CTC | GGG | CGT | CTG | ACC | AAG | 2236 |
| Glu 285 | Phe | Met | Ala | Ala | Asn 290 | Ala | Gly | Arg | Glu | Leu 295 | Gly | Arg | Leu | Thr | Lys 300 | |
| TAT | ACG | GGT | AAC | GCG | AGT | TCT | GTT | GTG | AAG | AGT | CAG | CTG | AGT | CGA | ATC | 2284 |
| Tyr | Thr | Gly | Asn | Ala 305 | Ser | Ser | Val | Val | Lys 310 | Ser | Gln | Leu | Ser | Arg 315 | Ile | |
| TTT | GAA | CAG | TAT | GAA | ATG | TAT | GGT | CGG | GGT | GAC | GCG | GTT | TGG | CTT | GCG | 2332 |
| Phe | Glu | Gln | Tyr 320 | Glu | Met | Tyr | Gly | Arg 325 | Gly | Asp | Ala | Val | Trp 330 | Leu | Ala | |
| GCG | GCG | GAC | ACC | GCC | TCA | TAT | TAC | GCA | GAT | TGT | AGT | GAG | TTC | GGA | ATT | 2380 |
| Ala | Ala | Asp | Thr 335 | Ala | Ser | Tyr | Tyr | Ala 340 | Asp | Cys | Ser | Glu | Phe 345 | Gly | Ile | |
| TGT | AAT | TTC | GAA | ACT | GAG | CTA | AAA | GGC | TTG | GTG | CTA | TCG | CAA | ACT | TAT | 2428 |
| Cys | Asn | Phe 350 | Glu | Thr | Glu | Leu | Lys 355 | Gly | Leu | Val | Leu | Ser 360 | Gln | Thr | Tyr | |
| ACT | TGT | AGC | CCG | ACA | ATC | CGA | ATT | TTG | TCT | CAG | AAT | ATG | ACG | CAA | GAG | 2476 |
| Thr | Cys | Ser | Pro | Thr | Ile | Arg | Ile | Leu | Ser | Gln | Asn | Met | Thr | Gln | Glu | |

-continued

| | | | | | | | | | | | | | | | |
|---|---|---|---|---|---|---|---|---|---|---|---|---|---|---|---|
| 365 | | | | | 370 | | | | | 375 | | | | 380 | |
| CAA | CAC | GCG | GCC | GCA | TGT | TCT | AAA | ATG | GGT | TAC | GAA | GAG | GGT | TAC | TTT | 2524
| Gln | His | Ala | Ala | Ala | Cys | Ser | Lys | Met | Gly | Tyr | Glu | Glu | Gly | Tyr | Phe |
| | | | 385 | | | | | 390 | | | | | | 395 | |
| CAT | CAG | TCA | TTA | GAA | ACT | GGT | GAA | CAG | CCA | GTA | AAA | GAT | GAC | CAC | AAT | 2572
| His | Gln | Ser | Leu | Glu | Thr | Gly | Glu | Gln | Pro | Val | Lys | Asp | Asp | His | Asn |
| | | | 400 | | | | | 405 | | | | | 410 | | |
| ACT | CAG | CTC | CAA | GTC | AAT | ATA | TTC | GAT | TCA | AGT | ACC | GAT | TAT | GGT | AAG | 2620
| Thr | Gln | Leu | Gln | Val | Asn | Ile | Phe | Asp | Ser | Ser | Thr | Asp | Tyr | Gly | Lys |
| | | 415 | | | | | 420 | | | | | 425 | | | |
| TAC | GCA | GGG | CCA | ATT | TTC | GAT | ATT | AGT | ACT | GAC | AAT | GGC | GGT | ATG | TAC | 2668
| Tyr | Ala | Gly | Pro | Ile | Phe | Asp | Ile | Ser | Thr | Asp | Asn | Gly | Gly | Met | Tyr |
| | 430 | | | | | 435 | | | | | 440 | | | | |
| TTG | GAG | GGC | GAC | CCT | TCC | CAG | CCG | GGG | AAT | ATT | CCC | AAC | TTT | ATT | GCT | 2716
| Leu | Glu | Gly | Asp | Pro | Ser | Gln | Pro | Gly | Asn | Ile | Pro | Asn | Phe | Ile | Ala |
| 445 | | | | | 450 | | | | | 455 | | | | | 460 |
| TAT | GAA | GCC | TCT | TAT | GCG | AAC | GCA | GAT | CAC | TTT | GTC | TGG | AAC | TTA | GAG | 2764
| Tyr | Glu | Ala | Ser | Tyr | Ala | Asn | Ala | Asp | His | Phe | Val | Trp | Asn | Leu | Glu |
| | | | | 465 | | | | | 470 | | | | | 475 | |
| CAC | GAA | TAC | GTG | CAT | TAC | TTA | GAT | GGT | CGA | TTT | GAT | CTC | TAT | GGA | GGG | 2812
| His | Glu | Tyr | Val | His | Tyr | Leu | Asp | Gly | Arg | Phe | Asp | Leu | Tyr | Gly | Gly |
| | | | 480 | | | | | 485 | | | | | 490 | | |
| TTT | AGT | CAT | CCA | ACT | GAA | AAA | ATA | GTG | TGG | TGG | AGT | GAA | GGC | ATT | GCA | 2860
| Phe | Ser | His | Pro | Thr | Glu | Lys | Ile | Val | Trp | Trp | Ser | Glu | Gly | Ile | Ala |
| | | 495 | | | | | 500 | | | | | 505 | | | |
| GAG | TAT | GTC | GCT | CAA | GAA | AAT | GAC | AAC | CAA | GCA | GCA | CTT | GAG | ACG | ATT | 2908
| Glu | Tyr | Val | Ala | Gln | Glu | Asn | Asp | Asn | Gln | Ala | Ala | Leu | Glu | Thr | Ile |
| | 510 | | | | | 515 | | | | | 520 | | | | |
| CTA | GAC | GGT | TCG | ACA | TAT | ACC | TTA | AGT | GAG | ATT | TTC | GAG | ACT | ACT | TAT | 2956
| Leu | Asp | Gly | Ser | Thr | Tyr | Thr | Leu | Ser | Glu | Ile | Phe | Glu | Thr | Thr | Tyr |
| 525 | | | | | 530 | | | | | 535 | | | | | 540 |
| GAT | GGG | TTT | GAT | GTC | GAT | CGA | ATT | TAT | CGT | TGG | GGG | TAC | TTA | GCT | GTA | 3004
| Asp | Gly | Phe | Asp | Val | Asp | Arg | Ile | Tyr | Arg | Trp | Gly | Tyr | Leu | Ala | Val |
| | | | | 545 | | | | | 550 | | | | | 555 | |
| CGT | TTT | ATG | TTT | GAA | AAT | CAT | AAA | GAT | GAC | GTA | AAC | CAA | ATG | CTG | GTG | 3052
| Arg | Phe | Met | Phe | Glu | Asn | His | Lys | Asp | Asp | Val | Asn | Gln | Met | Leu | Val |
| | | | 560 | | | | | 565 | | | | | 570 | | |
| GAA | ACA | CGC | CAA | GGG | AAT | TGG | ATC | AAT | TAC | AAG | GCC | ACG | ATC | ACC | CAA | 3100
| Glu | Thr | Arg | Gln | Gly | Asn | Trp | Ile | Asn | Tyr | Lys | Ala | Thr | Ile | Thr | Gln |
| | | 575 | | | | | 580 | | | | | 585 | | | |
| TGG | GCG | AAT | TTG | TAT | CAA | AGT | GAG | TTT | GAG | CAG | TGG | CAG | CAA | ACC | CTT | 3148
| Trp | Ala | Asn | Leu | Tyr | Gln | Ser | Glu | Phe | Glu | Gln | Trp | Gln | Gln | Thr | Leu |
| | 590 | | | | | 595 | | | | | 600 | | | | |
| GTC | TCA | AAT | GGT | GCT | CCT | AAT | GCA | GTC | ATA | ACC | GCA | AAC | AGT | AAG | GGG | 3196
| Val | Ser | Asn | Gly | Ala | Pro | Asn | Ala | Val | Ile | Thr | Ala | Asn | Ser | Lys | Gly |
| 605 | | | | | 610 | | | | | 615 | | | | | 620 |
| AAA | GTC | GGT | GAA | AGC | ATT | ACA | TTT | AGC | AGT | GAA | AAC | AGT | ACA | GAC | CCA | 3244
| Lys | Val | Gly | Glu | Ser | Ile | Thr | Phe | Ser | Ser | Glu | Asn | Ser | Thr | Asp | Pro |
| | | | | 625 | | | | | 630 | | | | | 635 | |
| AAC | GGG | AAG | ATC | GTC | AGC | GTC | TTA | TGG | GAC | TTC | GGT | GAT | GGC | TCG | ACA | 3292
| Asn | Gly | Lys | Ile | Val | Ser | Val | Leu | Trp | Asp | Phe | Gly | Asp | Gly | Ser | Thr |
| | | | 640 | | | | | 645 | | | | | 650 | | |
| AGT | ACA | CAA | ACC | AAG | CCG | ACG | CAC | CAA | TAT | GGG | AGT | GAA | GGG | GAG | TAT | 3340
| Ser | Thr | Gln | Thr | Lys | Pro | Thr | His | Gln | Tyr | Gly | Ser | Glu | Gly | Glu | Tyr |
| | | 655 | | | | | 660 | | | | | 665 | | | |
| TCG | GTC | AGC | CTA | AGT | GTG | ACA | GAC | AGT | GAA | GGC | TTG | ACG | GCA | ACC | GCC | 3388
| Ser | Val | Ser | Leu | Ser | Val | Thr | Asp | Ser | Glu | Gly | Leu | Thr | Ala | Thr | Ala |
| | 670 | | | | | 675 | | | | | 680 | | | | |
| ACT | CAT | ACT | GTT | GTT | ATC | TCA | GCG | TTG | GGC | GGT | AAT | GAC | ACA | TTG | CCA | 3436

| Thr | His | Thr | Val | Val | Ile | Ser | Ala | Leu | Gly | Gly | Asn | Asp | Thr | Leu | Pro |
| 685 | | | | | 690 | | | | | 695 | | | | | 700 |

| CAA | GAC | TGC | GCG | GTG | CAA | AGT | AAA | GTA | AGC | GGT | GGG | CGC | TTA | ACA | GCA | 3484 |
| Gln | Asp | Cys | Ala | Val | Gln | Ser | Lys | Val | Ser | Gly | Gly | Arg | Leu | Thr | Ala | |
| | | | | 705 | | | | | 710 | | | | | 715 | | |

| GGA | GAA | CCA | GTT | TGC | TTG | GCA | AAT | CAA | CAA | ACC | ATT | TGG | CTG | AGC | GTA | 3532 |
| Gly | Glu | Pro | Val | Cys | Leu | Ala | Asn | Gln | Gln | Thr | Ile | Trp | Leu | Ser | Val | |
| | | | 720 | | | | | 725 | | | | | 730 | | | |

| CCA | GCG | GTG | AAT | GAG | AGC | TCA | AAC | CTG | GCG | ATA | ACG | ACG | GGG | AAT | GGT | 3580 |
| Pro | Ala | Val | Asn | Glu | Ser | Ser | Asn | Leu | Ala | Ile | Thr | Thr | Gly | Asn | Gly | |
| | | 735 | | | | | 740 | | | | | 745 | | | | |

| ACG | GGC | AAC | CTA | AAG | CTT | GAA | TAC | AGT | AAC | TCT | GGT | TGG | CCG | GAT | GAT | 3628 |
| Thr | Gly | Asn | Leu | Lys | Leu | Glu | Tyr | Ser | Asn | Ser | Gly | Trp | Pro | Asp | Asp | |
| | 750 | | | | | 755 | | | | | 760 | | | | | |

| ACT | AAT | CTT | CAC | GGG | TGG | TCA | GAT | AAT | ATT | GGT | AAT | GGA | GAG | TGT | ATT | 3676 |
| Thr | Asn | Leu | His | Gly | Trp | Ser | Asp | Asn | Ile | Gly | Asn | Gly | Glu | Cys | Ile | |
| 765 | | | | 770 | | | | | 775 | | | | | 780 | | |

| ACG | TTG | TCA | AAT | CAG | AGT | AAC | TAC | TGG | GGC | TAC | GTT | AAA | GTC | TCT | GGT | 3724 |
| Thr | Leu | Ser | Asn | Gln | Ser | Asn | Tyr | Trp | Gly | Tyr | Val | Lys | Val | Ser | Gly | |
| | | | | 785 | | | | | 790 | | | | | 795 | | |

| GAC | TTT | GAG | AAT | GCC | GCC | ATC | GTC | GTT | GAT | TTT | GAT | GCT | CAG | AAG | TGT | 3772 |
| Asp | Phe | Glu | Asn | Ala | Ala | Ile | Val | Val | Asp | Phe | Asp | Ala | Gln | Lys | Cys | |
| | | | 800 | | | | | 805 | | | | | 810 | | | |

| CGT | CAG | TAGGGCAATT | TAACTACGTC | ATTAAACTA | AGTGGAGCGC | CTCGCTAACA | 3828 |
| Arg | Gln | | | | | | |

| TCGCGGGGGC | TTTTTGTTTT | TACGCCGTTA | TCTCTATAAA | AAAAACCAGC | CCGAAGGCTG | 3888 |
| GCAAACAAGA | AGTTTGAGAT | GAAAATGAAA | ACGTTATAAA | ACTTGCTGAT | ATCCTATTTC | 3948 |
| TCAATAAGTT | GGGTTGTGCT | TTGCAGCCAG | TTTTTATCTT | GCGCATCAAG | AAAAAGGGCT | 4008 |
| AAGCGCCTGA | TAGACACGTG | AATGGTAATG | ATTAAGCCAG | TCTCGC | | 4054 |

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:3:

```
AGT CAG CTG AGT CGA          15
Ser Gln Leu Ser Arg
 1               5
```

(2) INFORMATION FOR SEQ ID NO:4:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:

( K ) RELEVANT RESIDUES IN SEQ ID NO:

( x i ) SEQUENCE DESCRIPTION: SEQ ID NO:4:

| TAT | ACG | GGT | AAC | GCG | AGT | TCT | GTT | GTG | AAG | 30 |
|-----|-----|-----|-----|-----|-----|-----|-----|-----|-----|----|
| Tyr | Thr | Gly | Asn | Ala | Ser | Ser | Val | Val | Lys | |
| 1   |     |     |     | 5   |     |     |     |     | 10  | |

( 2 ) INFORMATION FOR SEQ ID NO:5:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:5:

| GCG | TCA | TCA | ATC | GGT | GCT | GAA | GAT | GAG | TTT | ATG | GCC | GCG | AAT | GCG | 45 |
|-----|-----|-----|-----|-----|-----|-----|-----|-----|-----|-----|-----|-----|-----|-----|----|
| Ala | Ser | Ser | Thr | Gly | Ala | Glu | Asp | Glu | Phe | Met | Ala | Ala | Asn | Ala | |
| 1   |     |     |     | 5   |     |     |     |     | 10  |     |     |     |     | 15  | |

| GGG | CGA | GAG | 54 |
|-----|-----|-----|----|
| Gly | Arg | Glu | |

( 2 ) INFORMATION FOR SEQ ID NO:6:

( i ) SEQUENCE CHARACTERISTICS:
        ( A ) LENGTH: 24 base pairs
        ( B ) TYPE: nucleic acid ( C ) STRANDEDNESS: single
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:6:

GAA  TCA  GTG  GAT  GCG  TTT  GTT  AAC            24
            Glu  Ser  Val  Asp  Ala  Phe  Val  Asn
            1                   5

( 2 ) INFORMATION FOR SEQ ID NO:7:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:

(F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:7:

```
CAA  GGG  AAT  TGG  ATC  AAT  TAC  AAG              24
Gln  Gly  Asn  Trp  Ile  Asn  Tyr  Lys
 1                 5
```

(2) INFORMATION FOR SEQ ID NO:8:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:

(C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:8:

| ATG | GGT | TAC | GAA | GAG | GGT | TAC | TTT | CAT | CAG | TCA | TTA | 36 |
|-----|-----|-----|-----|-----|-----|-----|-----|-----|-----|-----|-----|----|
| Met | Gly | Tyr | Glu | Glu | Gly | Tyr | Phe | His | Gln | Ser | Leu | |
| 1 | | | | 5 | | | | | 10 | | | |

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:9:

```
                        GCT  TTA  GGC  GAT  TTT  GCT  CTA  AGG           24
                        Ala  Leu  Gly  Asp  Phe  Ala  Leu  Arg
                         1                  5
```

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:10:

```
                        TGG  GGG  TAC  TTA  GCT  GTA  CGT                21
                        Trp  Gly  Tyr  Leu  Ala  Val  Arg
                         1                  5
```

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:11:

```
GCG  GGT  TAT  TAC  GCC  GAG                18
Ala  Gly  Tyr  Tyr  Ala  Glu
 1              5
```

( 2 ) INFORMATION FOR SEQ ID NO:12:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:

(A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:12:

```
          GTG   TGG   TGG   AGT   GAA                          15
          Val   Trp   Trp   Ser   Glu
           1                       5
```

(2) INFORMATION FOR SEQ ID NO:13:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:

( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:13:

```
TGG GTC ACC CCA GCG GTG AAA GAA                                    24
Trp Val Thr Pro Ala Val Lys Glu
 1               5
```

( 2 ) INFORMATION FOR SEQ ID NO:14:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:14:

```
TTA GAT GGT CGA TTT GAT CTC TAT GGA GGG TTT AGT CAT CCA ACT        45
Leu Asp Gly Arg Phe Asp Leu Tyr Gly Gly Phe Ser His Pro Thr
 1               5                  10                 15
GAA AAA                                                            51
```

Glu Lys (2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:15:

```
TAC AAT GAC AAC ATC TCA TTT                    21
Tyr Asn Glu Asn Ile Ser Phe
 1               5
```

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE:

(iii) HYPOTHETICAL:

(iv) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:16:

```
TCA  AGT  ACC  GAT  TAT  GGT  AAG  TAC  GCA  GGG  CCA  ATT  TTC  GAT         42
Ser  Ser  Thr  Glu  Tyr  Gly  Lys  Tyr  Ala  Gly  Pro  Ile  Phe  Glu
 1              5                        10
```

( 2 ) INFORMATION FOR SEQ ID NO:17:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

-continued (viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:17:

```
GGC  GAC  CCT  TCC  CAG  CCG  GGG  AAT  ATT  CCC  AAC  TTT  ATT  GCT  TAT  GAA     48
Gly  Asp  Pro  Ser  Gln  Pro  Gly  Asn  Ile  Pro  Asn  Phe  Ile  Ala  Tyr  Glu
 1                   5                        10                       15
```

(2) INFORMATION FOR SEQ ID NO:18:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:

(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:18:

```
TAC  GTG  CAT  TAC  TTA  GAT  GGT  CGA  TTT  GAT          30
Tyr  Val  His  Tyr  Leu  Asp  Gly  Arg  Phe  Asp
 1              5                         10
```

(2) INFORMATION FOR SEQ ID NO:19:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:19:

```
ACC  GCC  TCA  TAT  TAC  GCA  GAT  TGT  AGT  GAG          30
Thr  Ala  Ser  Tyr  Tyr  Ala  Asp  Cys  Ser  Glu
 1              5                         10
```

(2) INFORMATION FOR SEQ ID NO:20:

(i) SEQUENCE CHARACTERISTICS:

-continued

```
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:20:

TGG   AAT   GAT   CAA   TAC                               1 5
        Trp   Asn   Asp   Gln   Tyr
         1                       5

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
```

(D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:21:

GGG   TAT   ACG   GGT   GGC   GGG   AGC   GAT   GAA   CTA               30
            Gly   Tyr   Thr   Gly   Gly   Gly   Ser   Asp   Glu   Leu
             1                  5                              10

(2) INFORMATION FOR SEQ ID NO:22:

(i) SEQUENCE CHARACTERISTICS:
                (A) LENGTH: 739 amino acids
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:

(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:22:

```
Thr Ala Cys Asp Leu Glu Ala Leu Val Thr Glu Ser Ser Asn Gln Leu
 1               5                  10                  15
Ile Ser Glu Ile Leu Ser Gln Gly Ala Thr Cys Val Asn Gln Leu Phe
             20                  25                  30
Ser Ala Glu Ser Arg Ile Gln Glu Ser Val Phe Ser Ser Asp His Met
         35                  40                  45
Tyr Asn Ile Ala Lys His Thr Thr Leu Ala Lys Gly Tyr Thr Gly
 50                  55                  60
Gly Gly Ser Asp Glu Leu Glu Thr Leu Phe Leu Tyr Leu Arg Ala Gly
65                  70                  75                  80
Tyr Tyr Ala Glu Phe Tyr Asn Asp Asn Ile Ser Phe Ile Glu Trp Val
                 85                  90                  95
Thr Pro Ala Val Lys Glu Ser Val Asp Ala Phe Val Asn Thr Ala Ser
            100                 105                 110
Phe Tyr Glu Asn Ser Asp Arg His Gly Lys Val Leu Ser Glu Val Ile
        115                 120                 125
Ile Thr Met Asp Ser Ala Gly Leu Gln His Ala Tyr Leu Pro Gln Val
    130                 135                 140
Thr Gln Trp Leu Thr Arg Trp Asn Asp Gln Tyr Ala Gln His Trp Tyr
145                 150                 155                 160
Met Arg Asn Ala Val Asn Gly Val Phe Thr Ile Leu Phe Gly Gly Gln
                165                 170                 175
 Trp Asn Glu Gln Phe Val Gln Ile Ile Gly Asn Gln Thr Asp Leu Ala
            180                 185                 190
Lys Ala Leu Gly Asp Phe Ala Leu Arg Ala Ser Ser Ile Gly Ala Glu
        195                 200                 205
Asp Glu Phe Met Ala Ala Asn Ala Gly Arg Glu Leu Gly Arg Leu Thr
    210                 215                 220
Lys Tyr Thr Gly Asn Ala Ser Ser Val Val Lys Ser Gln Leu Ser Arg
225                 230                 235                 240
Ile Phe Glu Gln Tyr Glu Met Tyr Gly Arg Gly Asp Ala Val Trp Leu
                245                 250                 255
Ala Ala Ala Asp Thr Ala Ser Tyr Tyr Ala Asp Cys Ser Glu Phe Gly
            260                 265                 270
Ile Cys Asn Phe Glu Thr Glu Leu Lys Gly Leu Val Leu Ser Gln Thr
        275                 280                 285
Tyr Thr Cys Ser Pro Thr Ile Arg Ile Leu Ser Gln Asn Met Thr Gln
    290                 295                 300
Glu Gln His Ala Ala Ala Cys Ser Lys Met Gly Tyr Glu Glu Gly Tyr
305                 310                 315                 320
```

-continued

```
Phe His Gln Ser Leu Glu Thr Gly Glu Gln Pro Val Lys Asp Asp His
            325                 330                 335

Asn Thr Gln Leu Gln Val Asn Ile Phe Asp Ser Ser Thr Asp Tyr Gly
            340                 345                 350

Lys Tyr Ala Gly Pro Ile Phe Asp Ile Ser Thr Asp Asn Gly Gly Met
            355                 360                 365

Tyr Leu Glu Gly Asp Pro Ser Gln Pro Gly Asn Ile Pro Asn Phe Ile
370                 375                 380

Ala Tyr Glu Ala Ser Tyr Ala Asn Ala Asp His Phe Val Trp Asn Leu
385                 390                 395                 400

Glu His Glu Tyr Val His Tyr Leu Asp Gly Arg Phe Asp Leu Tyr Gly
            405                 410                 415

Gly Phe Ser His Pro Thr Glu Lys Ile Val Trp Trp Ser Glu Gly Ile
            420                 425                 430

Ala Glu Tyr Val Ala Gln Glu Asn Asp Asn Gln Ala Ala Leu Glu Thr
            435                 440                 445

Ile Leu Asp Gly Ser Thr Tyr Thr Leu Ser Glu Ile Phe Glu Thr Thr
     450                 455                 460

Tyr Asp Gly Phe Asp Val Asp Arg Ile Tyr Arg Trp Gly Tyr Leu Ala
465                 470                 475                 480

Val Arg Phe Met Phe Glu Asn His Lys Asp Asp Val Asn Gln Met Leu
            485                 490                 495

Val Glu Thr Arg Gln Gly Asn Trp Ile Asn Tyr Lys Ala Thr Ile Thr
            500                 505                 510

Gln Trp Ala Asn Leu Tyr Gln Ser Glu Phe Glu Gln Trp Gln Gln Thr
            515                 520                 525

Leu Val Ser Asn Gly Ala Pro Asn Ala Val Ile Thr Ala Asn Ser Lys
530                 535                 540

Gly Lys Val Gly Glu Ser Ile Thr Phe Ser Ser Glu Asn Ser Thr Asp
545                 550                 555                 560

Pro Asn Gly Lys Ile Val Ser Val Leu Trp Asp Phe Gly Asp Gly Ser
            565                 570                 575

Thr Ser Thr Gln Thr Lys Pro Thr His Gln Tyr Gly Ser Glu Gly Glu
            580                 585                 590

Tyr Ser Val Ser Leu Ser Val Thr Asp Ser Glu Gly Leu Thr Ala Thr
            595                 600                 605

Ala Thr His Thr Val Val Ile Ser Ala Leu Gly Gly Asn Asp Thr Leu
610                 615                 620

Pro Gln Asp Cys Ala Val Gln Ser Lys Val Ser Gly Gly Arg Leu Thr
625                 630                 635                 640

Ala Gly Glu Pro Val Cys Leu Ala Asn Gln Gln Thr Ile Trp Leu Ser
            645                 650                 655

Val Pro Ala Val Asn Glu Ser Ser Asn Leu Ala Ile Thr Thr Gly Asn
            660                 665                 670

Gly Thr Gly Asn Leu Lys Leu Glu Tyr Ser Asn Ser Gly Trp Pro Asp
            675                 680                 685

Asp Thr Asn Leu His Gly Trp Ser Asp Asn Ile Gly Asn Gly Glu Cys
            690                 695                 700

Ile Thr Leu Ser Asn Gln Ser Asn Tyr Trp Gly Tyr Val Lys Val Ser
705                 710                 715                 720

Gly Asp Phe Glu Asn Ala Ala Ile Val Val Asp Phe Asp Ala Gln Lys
            725                 730                 735
```

-continued

Cys Arg Gln (2) INFORMATION FOR SEQ ID NO:23:

(i) SEQUENCE CHARACTERISTICS:
        (A) LENGTH: 814 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:23:

```
Met Glu Leu Lys Ile Leu Ser Val Ala Ile Ala Thr Thr Leu Thr Ser
 1               5                  10                 15

Thr Gly Val Phe Ala Leu Ser Glu Pro Val Ser Gln Val Thr Glu Gln
                20                  25                 30

His Ala His Ser Ala His Thr His Gly Val Glu Phe Asn Arg Val Glu
                35                  40                 45

Tyr Gln Pro Thr Ala Thr Leu Pro Ile Gln Pro Ser Lys Ala Thr Arg
            50                  55                 60

Val Gln Ser Leu Glu Ser Leu Asp Glu Ser Ser
65                  70                 75

Thr Ala Cys Asp Leu Glu Ala Leu Val Thr Glu Ser Ser Asn Gln Leu
                80                  85                 90

Ile Ser Glu Ile Leu Ser Gln Gly Ala Thr Cys Val Asn Gln Leu Phe
```

95                          100                             105
Ser Ala Glu Ser Arg Ile Gln Glu Ser Val Phe Ser Ser Asp His Met
            110                     115                     120
Tyr Asn Ile Ala Lys His Thr Thr Leu Ala Lys Gly Tyr Thr Gly
        125                     130                 135
 Gly Gly Ser Asp Glu Leu Glu Thr Leu Phe Leu Tyr Leu Arg Ala Gly
140                     145                 150                     155
Tyr Tyr Ala Glu Phe Tyr Asn Asp Asn Ile Ser Phe Ile Glu Trp Val
                160                 165                     170
Thr Pro Ala Val Lys Glu Ser Val Asp Ala Phe Val Asn Thr Ala Ser
            175                 180                     185
Phe Tyr Glu Asn Ser Asp Arg His Gly Lys Val Leu Ser Glu Val Ile
        190                 195                     200
Ile Thr Met Asp Ser Ala Gly Leu Gln His Ala Tyr Leu Pro Gln Val
    205                     210                 215
Thr Gln Trp Leu Thr Arg Trp Asn Asp Gln Tyr Ala Gln His Trp Tyr
220                     225                 230                     235
Met Arg Asn Ala Val Asn Gly Val Phe Thr Ile Leu Phe Gly Gly Gln
                240                 245                     250
Tyr Asn Glu Gln Phe Val Gln Ile Ile Gly Asn Gln Thr Asp Leu Ala
            255                 260                     265
Lys Ala Leu Gly Asp Phe Ala Leu Arg Ala Ser Ser Ile Gly Ala Glu
        270                     275                 280
Asp Glu Phe Met Ala Ala Asn Ala Gly Arg Glu Leu Gly Arg Leu Thr
    285                     290                 295
Lys Tyr Thr Gly Asn Ala Ser Ser Val Val Lys Ser Gln Leu Ser Arg
300                     305                 310                     315
Ile Phe Glu Gln Tyr Glu Met Tyr Gly Arg Gly Asp Ala Val Trp Leu
                320                 325                     330
Ala Ala Ala Asp Thr Ala Ser Tyr Tyr Ala Asp Cys Ser Glu Phe Gly
            335                     340                 345
Ile Cys Asn Phe Glu Thr Glu Leu Lys Gly Leu Val Leu Ser Gln Thr
        350                     355                 360
Tyr Thr Cys Ser Pro Thr Ile Arg Ile Leu Ser Gln Asn Met Thr Gln
    365                     370                 375
Glu Gln His Ala Ala Ala Cys Ser Lys Met Gly Tyr Glu Glu Gly Tyr
380                     385                     390                 395
Phe His Gln Ser Leu Glu Thr Gly Glu Gln Pro Val Lys Asp Asp His
                400                     405                 410
 Asn Thr Gln Leu Gln Val Asn Ile Phe Asp Ser Ser Thr Asp Tyr Gly
            415                     420                 425
Lys Tyr Ala Gly Pro Ile Phe Asp Ile Ser Thr Asp Asn Gly Gly Met
        430                     435                 440
Tyr Leu Glu Gly Asp Pro Ser Gln Pro Gly Asn Ile Pro Asn Phe Ile
    445                     450                 455
Ala Tyr Glu Ala Ser Tyr Ala Asn Ala Asp His Phe Val Trp Asn Leu
460                     465                     470                 475
Glu His Glu Tyr Val His Tyr Leu Asp Gly Arg Phe Asp Leu Tyr Gly
                480                     485                 490
Gly Phe Ser His Pro Thr Glu Lys Ile Val Trp Trp Ser Glu Gly Ile
            495                     500                 505
Ala Glu Tyr Val Ala Gln Glu Asn Asp Asn Gln Ala Ala Leu Glu Thr
        510                     515                 520

```
Ile  Leu  Asp  Gly  Ser  Thr  Tyr  Thr  Leu  Ser  Glu  Ile  Phe  Glu  Thr  Thr
     525                      530                     535

Tyr  Asp  Gly  Phe  Asp  Val  Asp  Arg  Ile  Tyr  Arg  Trp  Gly  Tyr  Leu  Ala
540                      545                     550                          555

Val  Arg  Phe  Met  Phe  Glu  Asn  His  Lys  Asp  Asp  Val  Asn  Gln  Met  Leu
               560                      565                          570

Val  Glu  Thr  Arg  Gln  Gly  Asn  Trp  Ile  Asn  Tyr  Lys  Ala  Thr  Ile  Thr
               575                      580                     585

Gln  Trp  Ala  Asn  Leu  Tyr  Gln  Ser  Glu  Phe  Glu  Gln  Trp  Gln  Gln  Thr
          590                      595                          600

Leu  Val  Ser  Asn  Gly  Ala  Pro  Asn  Ala  Val  Ile  Thr  Ala  Asn  Ser  Lys
     605                      610                     615

Gly  Lys  Val  Gly  Glu  Ser  Ile  Thr  Phe  Ser  Ser  Glu  Asn  Ser  Thr  Asp
620                      625                     630                          635

Pro  Asn  Gly  Lys  Ile  Val  Ser  Val  Leu  Trp  Asp  Phe  Gly  Asp  Gly  Ser
               640                      645                          650

Thr  Ser  Thr  Gln  Thr  Lys  Pro  Thr  His  Gln  Tyr  Gly  Ser  Glu  Gly  Glu
               655                      660                          665

Tyr  Ser  Val  Ser  Leu  Ser  Val  Thr  Asp  Ser  Glu  Gly  Leu  Thr  Ala  Thr
               670                      675                          680

Ala  Thr  His  Thr  Val  Val  Ile  Ser  Ala  Leu  Gly  Gly  Asn  Asp  Thr  Leu
      685                      690                     695

Pro  Gln  Asp  Cys  Ala  Val  Gln  Ser  Lys  Val  Ser  Gly  Gly  Arg  Leu  Thr
700                      705                     710                          715

Ala  Gly  Glu  Pro  Val  Cys  Leu  Ala  Asn  Gln  Gln  Thr  Ile  Trp  Leu  Ser
               720                      725                          730

Val  Pro  Ala  Val  Asn  Glu  Ser  Ser  Asn  Leu  Ala  Ile  Thr  Thr  Gly  Asn
               735                      740                          745

Gly  Thr  Gly  Asn  Leu  Lys  Leu  Glu  Tyr  Ser  Asn  Ser  Gly  Trp  Pro  Asp
          750                      755                          760

Asp  Thr  Asn  Leu  His  Gly  Trp  Ser  Asp  Asn  Ile  Gly  Asn  Gly  Glu  Cys
     765                      770                     775

Ile  Thr  Leu  Ser  Asn  Gln  Ser  Asn  Tyr  Trp  Gly  Tyr  Val  Lys  Val  Ser
780                      785                     790                          795

Gly  Asp  Phe  Glu  Asn  Ala  Ala  Ile  Val  Val  Asp  Phe  Asp  Ala  Gln  Lys
               800                      805                          810

Cys  Arg  Gln
```

( 2 ) INFORMATION FOR SEQ ID NO:24:

( i ) SEQUENCE CHARACTERISTICS:
        ( A ) LENGTH: 2217 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:

( E ) HAPLOTYPE:
( F ) TISSUE TYPE:
( G ) CELL TYPE:
( H ) CELL LINE:
( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:24:

```
ACTGCTTGTG ATTTGGAGGC ATTGGTTACC GAAAGCAGTA ACCAATTGAT CAGCGAAATT    60
TTAAGTCAGG GCGCGACGTG TGTGAACCAG TTATTCTCTG CTGAAAGTCG GATTCAAGAG   120
TCGGTATTTA GCTCCGATCA TATGTACAAC ATCGCTAAGC ACACTACGAC GTTGGCGAAG   180
GGGTATACGG GTGGCGGGAG CGATGAACTA GAAACGTTGT TCTTATACTT ACGCGCGGGT   240
TATTACGCCG AGTTTTACAA TGACAACATC TCATTTATTG AATGGGTCAC CCCAGCGGTG   300
AAAGAATCAG TGGATGCGTT TGTTAACACA GCAAGCTTCT ACGAGAACAG CGACCGTCAC   360
GGCAAAGTGC TTAGTGAGGT CATCATCACT ATGGATAGTG CGGGCTTGCA GCACGCGTAC   420
TTACCGCAAG TGACCCAGTG GCTTACTCGT TGGAATGATC AATACGCCCA GCACTGGTAT   480
ATGCGCAATG CGGTTAACGG TGTTTTCACT ATTTTGTTTG GTGGGCAGTG GAACGAGCAA   540
TTTGTGCAAA TAATTGGCAA CCAAACGGAC CTTGCCAAAG CTTTAGGCGA TTTTGCTCTA   600
AGGGCGTCAT CAATCGGTGC TGAAGATGAG TTTATGGCCG CGAATGCGGG GCGAGAGCTC   660
GGGCGTCTGA CCAAGTATAC GGGTAACGCG AGTTCTGTTG TGAAGAGTCA GCTGAGTCGA   720
ATCTTTGAAC AGTATGAAAT GTATGGTCGG GGTGACGCGG TTTGGCTTGC GGCGGCGGAC   780
ACCGCCTCAT ATTACGCAGA TTGTAGTGAG TTCGGAATTT GTAATTCGA AACTGAGCTA    840
AAAGGCTTGG TGCTATCGCA AACTTATACT TGTAGCCCGA CAATCCGAAT TTTGTCTCAG   900
AATATGACGC AAGAGCAACA CGCGGCCGCA TGTTCTAAAA TGGGTTACGA AGAGGGTTAC   960
TTTCATCAGT CATTAGAAAC TGGTGAACAG CCAGTAAAAG ATGACCACAA TACTCAGCTC  1020
CAAGTCAATA TATTCGATTC AAGTACCGAT TATGGTAAGT ACGCAGGGCC AATTTTCGAT  1080
ATTAGTACTG ACAATGGCGG TATGTACTTG GAGGGCGACC CTTCCCAGCC GGGGAATATT  1140
CCCAACTTTA TTGCTTATGA AGCCTCTTAT GCGAACGCAG ATCACTTTGT CTGGAACTTA  1200
GAGCACGAAT ACGTGCATTA CTTAGATGGT CGATTTGATC TCTATGGAGG GTTTAGTCAT  1260
CCAACTGAAA AAATAGTGTG GTGGAGTGAA GGCATTGCAG AGTATGTCGC TCAAGAAAAT  1320
```

```
GACAACCAAG  CAGCACTTGA  GACGATTCTA  GACGGTTCGA  CATATACCTT  AAGTGAGATT       1380

TTCGAGACTA  CTTATGATGG  GTTTGATGTC  GATCGAATTT  ATCGTTGGGG  GTACTTAGCT       1440

GTACGTTTTA  TGTTTGAAAA  TCATAAAGAT  GACGTAAACC  AAATGCTGGT  GGAAACACGC       1500

CAAGGGAATT  GGATCAATTA  CAAGGCCACG  ATCACCCAAT  GGGCGAATTT  GTATCAAAGT       1560

GAGTTTGAGC  AGTGGCAGCA  AACCCTTGTC  TCAAATGGTG  CTCCTAATGC  AGTCATAACC       1620

GCAAACAGTA  AGGGGAAAGT  CGGTGAAAGC  ATTACATTTA  GCAGTGAAAA  CAGTACAGAC       1680

CCAAACGGGA  AGATCGTCAG  CGTCTTATGG  GACTTCGGTG  ATGGCTCGAC  AAGTACACAA       1740

ACCAAGCCGA  CGCACCAATA  TGGGAGTGAA  GGGGAGTATT  CGGTCAGCCT  AAGTGTGACA       1800

GACAGTGAAG  GCTTGACGGC  AACCGCCACT  CATACTGTTG  TTATCTCAGC  GTTGGGCGGT       1860

AATGACACAT  TGCCACAAGA  CTGCGCGGTG  CAAAGTAAAG  TAAGCGGTGG  GCGCTTAACA      1920

GCAGGAGAAC  CAGTTTGCTT  GGCAAATCAA  CAAACCATTT  GGCTGAGCGT  ACCAGCGGTG       1980

AATGAGAGCT  CAAACCTGGC  GATAACGACG  GGGAATGGTA  CGGGCAACCT  AAAGCTTGAA       2040

TACAGTAACT  CTGGTTGGCC  GGATGATACT  AATCTTCACG  GGTGGTCAGA  TAATATTGGT       2100

AATGGAGAGT  GTATTACGTT  GTCAAATCAG  AGTAACTACT  GGGGCTACGT  TAAAGTCTCT       2160

GGTGACTTTG  AGAATGCCGC  CATCGTCGTT  GATTTGATG   CTCAGAAGTG  TCGTCAG         2217
```

( 2 ) INFORMATION FOR SEQ ID NO:25:

( i ) SEQUENCE CHARACTERISTICS:
        ( A ) LENGTH: 2442 base pairs
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:

( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:25:

| | | | | | | |
|---|---|---|---|---|---|---|
| ATGGAACTGA | AGATTTTGAG | TGTCGCGATT | GCGACAACAT | TAACCAGCAC | TGGCGTATTT | 60 |
| GCGTTAAGCG | AGCCAGTTTC | TCAAGTTACA | GAGCAACATG | CACATTCGGC | TCATACACAC | 120 |
| GGTGTTGAAT | TCAATCGAGT | TGAATACCAA | CCAACCGCAA | CTCTCCCAAT | TCAGCCCTCT | 180 |
| AAGGCAACTC | GAGTACAGTC | ACTTGAAAGC | CTTGATGAGT | CGAGC | | 225 |
| ACTGCTTGTG | ATTTGGAGGC | ATTGGTTACC | GAAAGCAGTA | ACCAATTGAT | CAGCGAAATT | 285 |
| TTAAGTCAGG | GCGCGACGTG | TGTGAACCAG | TTATTCTCTG | CTGAAAGTCG | GATTCAAGAG | 345 |
| TCGGTATTTA | GCTCCGATCA | TATGTACAAC | ATCGCTAAGC | ACACTACGAC | GTTGGCGAAG | 405 |
| GGGTATACGG | GTGGCGGGAG | CGATGAACTA | GAAACGTTGT | TCTTATACTT | ACGCGCGGGT | 465 |
| TATTACGCCG | AGTTTTACAA | TGACAACATC | TCATTTATTG | AATGGGTCAC | CCCAGCGGTG | 525 |
| AAAGAATCAG | TGGATGCGTT | TGTTAACACA | GCAAGCTTCT | ACGAGAACAG | CGACCGTCAC | 585 |
| GGCAAAGTGC | TTAGTGAGGT | CATCATCACT | ATGGATAGTG | CGGGCTTGCA | GCACGCGTAC | 645 |
| TTACCGCAAG | TGACCCAGTG | GCTTACTCGT | TGGAATGATC | AATACGCCCA | GCACTGGTAT | 705 |
| ATGCGCAATG | CGGTTAACGG | TGTTTTCACT | ATTTGTTTG | GTGGGCAGTG | GAACGAGCAA | 765 |
| TTTGTGCAAA | TAATTGGCAA | CCAAACGGAC | CTTGCCAAAG | CTTTAGGCGA | TTTTGCTCTA | 825 |
| AGGGCGTCAT | CAATCGGTGC | TGAAGATGAG | TTTATGGCCG | CGAATGCGGG | GCGAGAGCTC | 885 |
| GGGCGTCTGA | CCAAGTATAC | GGGTAACGCG | AGTTCTGTTG | TGAAGAGTCA | GCTGAGTCGA | 945 |
| ATCTTTGAAC | AGTATGAAAT | GTATGGTCGG | GGTGACGCGG | TTTGGCTTGC | GGCGGCGGAC | 1005 |
| ACCGCCTCAT | ATTACGCAGA | TTGTAGTGAG | TTCGGAATTT | GTAATTTCGA | AACTGAGCTA | 1065 |
| AAAGGCTTGG | TGCTATCGCA | AACTTATACT | TGTAGCCCGA | CAATCCGAAT | TTTGTCTCAG | 1125 |
| AATATGACGC | AAGAGCAACA | CGCGGCCGCA | TGTTCTAAAA | TGGGTTACGA | AGAGGGTTAC | 1185 |
| TTTCATCAGT | CATTAGAAAC | TGGTGAACAG | CCAGTAAAAG | ATGACCACAA | TACTCAGCTC | 1245 |
| CAAGTCAATA | TATTCGATTC | AAGTACCGAT | TATGGTAAGT | ACGCAGGGCC | AATTTTCGAT | 1305 |
| ATTAGTACTG | ACAATGGCGG | TATGTACTTG | GAGGGCGACC | CTTCCCAGCC | GGGGAATATT | 1365 |
| CCCAACTTTA | TTGCTTATGA | AGCCTCTTAT | GCGAACGCAG | ATCACTTTGT | CTGGAACTTA | 1425 |
| GAGCACGAAT | ACGTGCATTA | CTTAGATGGT | CGATTTGATC | TCTATGGAGG | GTTTAGTCAT | 1485 |
| CCAACTGAAA | AATAGTGTG | GTGGAGTGAA | GGCATTGCAG | AGTATGTCGC | TCAAGAAAAT | 1545 |
| GACAACCAAG | CAGCACTTGA | GACGATTCTA | GACGGTTCGA | CATATACCTT | AAGTGAGATT | 1605 |
| TTCGAGACTA | CTTATGATGG | GTTTGATGTC | GATCGAATTT | ATCGTTGGGG | GTACTTAGCT | 1665 |
| GTACGTTTTA | TGTTTGAAAA | TCATAAAGAT | GACGTAAACC | AAATGCTGGT | GGAAACACGC | 1725 |
| CAAGGGAATT | GGATCAATTA | CAAGGCCACG | ATCACCCAAT | GGGCGAATTT | GTATCAAAGT | 1785 |
| GAGTTTGAGC | AGTGGCAGCA | AACCCTTGTC | TCAAATGGTG | CTCCTAATGC | AGTCATAACC | 1845 |
| GCAAACAGTA | AGGGGAAAGT | CGGTGAAAGC | ATTACATTTA | GCAGTGAAAA | CAGTACAGAC | 1905 |
| CCAAACGGGA | AGATCGTCAG | CGTCTTATGG | GACTTCGGTG | ATGGCTCGAC | AAGTACACAA | 1965 |
| ACCAAGCCGA | CGCACCAATA | TGGGAGTGAA | GGGGAGTATT | CGGTCAGCCT | AAGTGTGACA | 2025 |
| GACAGTGAAG | GCTTGACGGC | AACCGCCACT | CATACTGTTG | TTATCTCAGC | GTTGGGCGGT | 2085 |

| | | | | | | |
|---|---|---|---|---|---|---|
| AATGACACAT | TGCCACAAGA | CTGCGCGGTG | CAAAGTAAAG | TAAGCGGTGG | GCGCTTAACA | 2145 |
| GCAGGAGAAC | CAGTTTGCTT | GGCAAATCAA | CAAACCATTT | GGCTGAGCGT | ACCAGCGGTG | 2205 |
| AATGAGAGCT | CAAACCTGGC | GATAACGACG | GGGAATGGTA | CGGGCAACCT | AAAGCTTGAA | 2265 |
| TACAGTAACT | CTGGTTGGCC | GGATGATACT | AATCTTCACG | GGTGGTCAGA | TAATATTGGT | 2325 |
| AATGGAGAGT | GTATTACGTT | GTCAAATCAG | AGTAACTACT | GGGGCTACGT | TAAAGTCTCT | 2385 |
| GGTGACTTTG | AGAATGCCGC | CATCGTCGTT | GATTTGATG | CTCAGAAGTG | TCGTCAG | 2442 |

What is claimed is:

1. An isolated and purified gene encoding a collagenase of *Vibrio alginolyticus* and having a restriction map as shown in FIG. 1.

2. A recombinant vector comprising the gene of claim 1.

3. An *E. coli* host cell transformed with a plasmid comprising the gene of claim 1.

4. A process for the production of a collagenase which comprises cultivating the *E. coli* host cell of claim 3 to express the collagenase, and recovering the collagenase.

5. The gene according to claim 1, which is the 2.7 kb HpaI-EcoRV fragment shown in the restriction map of FIG. 1.

6. A recombinant vector comprising the gene of claim 5.

7. An *E. coli* host cell transformed with a plasmid comprising the gene of claim 5.

8. A process for the production of a collagenase which comprises cultivating the *E. coli* cell of claim 7 to express the collagenase, and recovering the collagenase.

9. The gene according to claim 5, wherein said collagenase comprises peptide fragments of the formulas (a) to (t), the peptide fragments of the formulas (a) and (c) to (t) being shown in SEQ ID Nos. 3–21:
(a): S Q L S R
(b): I Y R
(c): Y T G N A S S V V K
(d): A S S I G A E D E F M A A N A G R E
(e): E S V D A F V N
(f): Q G N W I N Y K
(g): M G Y E E G Y F H Q S L
(h): A L G D F A L R
(i): W G Y L A V R
(j): A G Y Y A E
(k): V W W S E
(l): W V T P A V K E
(m): L D G R F D L Y G G F S H P T E K
(n): Y N D N I S F
(o): S S T D Y G K Y A G P I F D
(p): G D P S Q P G N I P N F I A Y E
(q): Y V H Y L D G R F D
(r): T A S Y Y A D C S E
(s): W N D Q Y
(t): G Y T G G G S D E L
wherein A is alanine, C is cysteine, D is aspartic acid, E is glutamic acid, F is phenylalanine, G is glycine, H is histidine, I is isoleucine, K is lysine, L is leucine, M is methionine, N is asparagine, P is proline, Q is glutamine, R is arginine, S is serine, T is threonine, V is valine, W is tryptophan and Y is tyrosine.

10. An isolated and purified gene encoding a collagenase having an amino acid sequence comprising the amino acid sequence of the following formula as shown in SEQ ID No. 22:

X—

TACDLEALVTESSNQLISEILSQGATCVNQLFSAESRIQE

SYFSSDHMYNIAKHTTTLAKGYTGGGSDELETLFLYLRAG

YYAEFYNDNISFIEWVTPAYKESVDAFYNTASFYENSDRH

GKYLSEVIITMDSAGLQHAYLPQVTQWLTRWNDQYAQHWY

MRNAVNGVFTILFGGQWNEQFYQIIGNQTDLAKALGDFAL

RASSIGAEDEFMAANAGRELGRLTKYTGNASSYYKSQLSR

IFEQYEMYGRGDAVWLAAADTASYYADCSEFGICNFETEL

KGLVLSQTYTCSPTIRILSQNMTQEQHAAACSKMGYEEGY

FHQSLETGEQPVKDDHNTQLQVNIFDSSTDYGKYAGPIFD

ISTDNGGMYLEGDPSQPGNIPHFIAYEASYANADHFYWNL

EHEYVHYLDGRFDLYGGFSHPTEKIVWWSEGIAEYVAQEN

DNQAALETILDGSTYTLSEIFETTYDGFDVDRIYRWGYLA

VRFMFENHKDDVNQMLVETRQGNWINYKATITQWANLYQS

-continued

EFEQWQQTLYSNGAPNAVITANSKGKVGESITFSSENSTD

PNGKIYSYLWDFGDGSTSTQTKPTHQYGSEGEYSVSLSVT

DSEGLTATATHTVVISALGGNDTLPQDCAVQSKVSGGRLT

AGEPVCLANQQTIWLSVPAVNESSNLAITTGNGTGNLKLE

YSNSGWPDDTNLHGWSDNIGNGECITLSNQSNYWGYVKVS

GDFENAAIVVDFDAQKCRQ wherein X is hydrogen, and
wherein A is alanine, C is cysteine, D is aspartic acid, E is glutamic acid, F is phenylalanine, G is glycine, H is histidine, I is isoleucine, K is lysine, L is leucine, M is methionine, N is asparagine, P is proline, Q is glutamine, R is arginine, S is serine, T is threonine, V is valine, W is tryptophan and Y is tyrosine.

11. An isolated and purified gene encoding a collagenase having an amino acid sequence consisting of the amino acid sequence of the following formula as shown in SEQ ID No. 22:

X—

TACDLEALVTESSNQLISEILSQGATCVNQLFSAESRIQE

SYFSSDHMYNIAKHTTTLAKGYTGGGSDELETLFLYLRAG

YYAEFYNDNISFIEWVTPAYKESVDAFYNTASFYENSDRH

GKYLSEVIITMDSAGLQHAYLPQVTQWLTRWNDQYAQHWY

MRNAVNGVFTILFGGQWNEQFYQIIGNQTDLAKALGDFAL

RASSIGAEDEFMAANAGRELGRLTKYTGNASSYYKSQLSR

IFEQYEMYGRGDAVWLAAADTASYYADCSEFGICNFETEL

KGLVLSQTYTCSPTIRILSQNMTQEQHAAACSKMGYEEGY

FHQSLETGEQPVKDDHNTQLQVNIFDSSTDYGKYAGPIFD

ISTDNGGMYLEGDPSQPGNIPHFIAYEASYANADHFYWNL

EHEYVHYLDGRFDLYGGFSHPTEKIVWWSEGIAEYVAQEN

DNQAALETILDGSTYTLSEIFETTYDGFDVDRIYRWGYLA

VRFMFENHKDDVNQMLVETRQGNWINYKATITQWANLYQS

EFEQWQQTLYSNGAPNAVITANSKGKVGESITFSSENSTD

PNGKIYSYLWDFGDGSTSTQTKPTHQYGSEGEYSVSLSVT

DSEGLTATATHTVVISALGGNDTLPQDCAVQSKVSGGRLT

AGEPVCLANQQTIWLSVPAVNESSNLAITTGNGTGNLKLE

YSNSGWPDDTNLHGWSDNIGNGECITLSNQSNYWGYVKVS

GDFENAAIVVDFDAQKCRQ wherein X is hydrogen, and
wherein A is alanine, C is cysteine, D is aspartic acid, E is glutamic acid, F is phenylalanine, G is glycine, H is histidine, I is isoleucine, K is lysine, L is leucine, M is methionine, N is asparagine, P is proline, Q is glutamine, R is arginine, S is serine, T is threonine, V is valine, W is tryptophan and Y is tyrosine.

12. A recombinant vector comprising the gene of claim 10 or 11.

13. An *E. coli* host cell transformed with a plasmid comprising the gene of claim 10 or 11.

14. A process for the production of a collagenase which comprises cultivating the host cells of claim 13 to express the collagenase, and recovering the collagenase.

15. An isolated and purified gene encoding a collagenase precursor having an amino acid sequence comprising the amino acid sequence of the following formula as shown in SEQ ID No. 23:

X—

TACDLEALVTESSNQLISEILSQGATCVNQLFSAESRIQE

SYFSSDHMYNIAKHTTTLAKGYTGGGSDELETLFLYLRAG

YYAEFYNDNISFIEWVTPAYKESVDAFYNTASFYENSDRH

GKYLSEVIITMDSAGLQHAYLPQVTQWLTRWNDQYAQHWY

MRNAVNGVFTILFGGQWNEQFYQIIGNQTDLAKALGDFAL

RASSIGAEDEFMAANAGRELGRLTKYTGNASSYYKSQLSR

IFEQYEMYGRGDAVWLAAADTASYYADCSEFGICNFETEL

KGLVLSQTYTCSPTIRILSQNMTQEQHAAACSKMGYEEGY

FHQSLETGEQPVKDDHNTQLQVNIFDSSTDYGKYAGPIFD

ISTDNGGMYLEGDPSQPGNIPHFIAYEASYANADHFYWNL

EHEYVHYLDGRFDLYGGFSHPTEKIVWWSEGIAEYVAQEN

DNQAALETILDGSTYTLSEIFETTYDGFDVDRIYRWGYLA

VRFMFENHKDDVNQMLVETRQGNWINYKATITQWANLYQS

EFEQWQQTLYSNGAPNAVITANSKGKVGESITFSSENSTD

PNGKIYSYLWDFGDGSTSTQTKPTHQYGSEGEYSVSLSVT

DSEGLTATATHTVVISALGGNDTLPQDCAVQSKVSGGRLT

AGEPVCLANQQTIWLSVPAVNESSNLAITTGNGTGNLKLE

YSNSGWPDDTNLHGWSDNIGNGECITLSNQSNYWGYVKVS

GDFENAAIVVDFDAQKCRQ wherein X is a polypeptide of the formula:

MELKILSVAIATTLTSTGVFALSEPVSQVTEQHAHSAHTH

GVEFNRVEYQPTATLPIQPSKATRVQSLESLDESS and wherein A is alanine, C is cysteine, D is aspartic acid, E is glutamic acid, F is phenylalanine, G is glycine, H is histidine, I is isoleucine, K is lysine, L is leucine, M is methionine, N is asparagine, P is proline, Q is glutamine, R is arginine, S is serine, T is threonine, V is valine, W is tryptophan and Y is tyrosine.

16. An isolated and purified gene encoding a collagenase precursor having an amino acid sequence consisting of the amino acid sequence of the following formula as shown in SEQ ID No. 23:

X—

TACDLEALVTESSNQLISEILSQGATCVNQLFSAESRIQE

SYFSSDHMYNIAKHTTTLAKGYTGGGSDELETLFLYLRAG

YYAEFYNDNISFIEWVTPAYKESVDAFYNTASFYENSDRH

GKYLSEVIITMDSAGLQHAYLPQVTQWLTRWNDQYAQHWY

MRNAVNGVFTILFGGQWNEQFYQIIGNQTDLAKALGDFAL

RASSIGAEDEFMAANAGRELGRLTKYTGNASSYYKSQLSR

IFEQYEMYGRGDAVWLAAADTASYYADCSEFGICNFETEL

KGLVLSQTYTCSPTIRILSQNMTQEQHAAACSKMGYEEGY

FHQSLETGEQPVKDDHNTQLQVNIFDSSTDYGKYAGPIFD

ISTDNGGMYLEGDPSQPGNIPHFIAYEASYANADHFYWNL

EHEYVHYLDGRFDLYGGFSHPTEKIVWWSEGIAEYVAQEN

DNQAALETILDGSTYTLSEIFETTYDGFDVDRIYRWGYLA

VRFMFENHKDDVNQMLVETRQGNWINYKATITQWANLYQS

EFEQWQQTLYSNGAPNAVITANSKGKVGESITFSSENSTD

PNGKIYSYLWDFGDGSTSTQTKPTHQYGSEGEYSVSLSVT

DSEGLTATATHTVVISALGGNDTLPQDCAVQSKVSGGRLT

AGEPVCLANQQTIWLSVPAVNESSNLAITTGNGTGNLKLE

YSNSGWPDDTNLHGWSDNIGNGECITLSNQSNYWGYVKVS

GDFENAAIVVDFDAQKCRQ wherein X is a polypeptide of the formula:

MELKILSVAIATTLTSTGVFALSEPVSQVTEQHAHSAHTH

GVEFNRVEYQPTATLPIQPSKATRVQSLESLDESS and wherein A is alanine, C is cysteine, D is aspartic acid, E is glutamic acid, F is phenylalanine, G is glycine, H is histidine, I is isoleucine, K is lysine, L is leucine, M is methionine, N is asparagine, P is proline, Q is glutamine, R is arginine, S is serine, T is threonine, V is valine, W is tryptophan and Y is tryosine.

17. A recombinant vector comprising the gene of claim 15 or 16.

18. An *E. coli* host cell transformed with a plasmid comprising the gene of claim 15 or 16.

19. A process for the production of a collagenase which comprises cultivating the host cells of claim 18 to express the collagenase, and recovering the collagenase.

20. An isolated and purified gene encoding a collagenase of *Vibrio alginolyticus* which comprises a DNA sequence of the following formula as shown in SEQ ID No. 24:

Z—

ACTGCTTGTGATTTGGAGGCATTGGTTACCGAAAGCAGTAACCA

ATTGATCAGCGAAATTTTAAGTCAGGGCGCGACGTGTGTGAACC

AGTTATTCTCTGCTGAAAGTCGGATTCAAGAGTCGGTATTTACC

TCCGATCATATGTACAACATCGCTAAGCACACTACGACGTTGGC

GAAGGGGTATACGGGTGGCGGGAGCGATGAACTAGAAACGTTGT

TCTTATACTTACGCGCGGGTTATTACGCCGAGTTTTACAATGAC

AACATCTCATTTATTGAATGGGTCACCCCAGCGGTGAAAGAATC

AGTGGATGCGTTTGTTAACACAGCAAGCTTCTACGAGAACAGCG

ACCGTCACGGCAAAGTGCTTAGTGAGGTCATCATCACTATGGAT

AGTGCGGGCTTGCAGCACGCGTACTTACCGCAAGTGACCCAGTG

GCTTACTCGTTGGAATGATCAATACGCCCAGCACTGGTATATGC

GCAATGCGGTTAACGGTGTTTTCACTATTTTGTTTGGTGGGCAG

TGGAACGAGCAATTTGTGCAAATAATTGGCAACCAAACGGACCT

TGCCAAAGCTTTAGGCGATTTTGCTCTAAGGGCGTCATCAATCG

GTGCTGAAGATGAGTTTATGGCCCCGAATGCGGGGCGAGAGCTC

GGGCGTCTGACCAAGTATACGGCTAACGCGAGTTCTGTTGTGAA

GAGTCAGCTGAGTCGAATCTTTGAACAGTATGAAATGTATGGTC

GGGGTGACGCGGTTTGGCTTGCGGCGGCGGACACCGCCTCATAT

TACGCAGATTGTAGTGAGTTCGGAATTTGTAATTTCGAAACTGA

GCTAAAAGGCTTGGTGCTATCGCAAACTTATACTTGTAGCCCGA

CAATCCGAATTTTGTCTCAGAATATGACGCAAGAGCAACACGCG

GCCGCATGTTCTAAAATGGGTTACGAAGAGGGTTACTTTCATCA

GTCATTAGAAACTGGTGAACAGCCAGTAAAAGATGACCACAATA

CTCAGCTCCAAGTCAATATATTCGATTCAAGTACCGATTATGGT

AAGTACGCAGGGCCAATTTTCGATATTAGTACTGACAATGGCGG

TATGTACTTGGAGGGCGACCCTTCCCAGCCGGGGAATATTCCCA

ACTTTATTGCTTATGAACCCTCTTATGCGAACGCAGATCACTTT

GTCTGGAACTTAGAGCACGAATACGTGCATTACTTAGATGGTCG

ATTTGATCTCTATGGAGGGTTTAGTCATCCAACTGAAAAAATAG

TGTGGTGGAGTGAAGGCATTGCAGAGTATGTCGCTCAAGAAAAT

GACAACCAAGCAGCACTTGAGACGATTCTAGACGGTTCGACATA

TACCTTAAGTGAGATTTTCGAGACTACTTATGATGGGTTTGATG

TCGATCGAATTTATCGTTGGGGGTACTTAGCTGTACGTTTTATG

TTTGAAAATCATAAAGATGACGTAAACCAAATGCTGGTGGAAAC

ACGCCAAGGGAATTGGATCAATTACAAGGCCACGATCACCCAAT

GGGCGAATTTGTATCAAAGTGAGTTTGAGCAGTGGCAGCAAACC

CTTGTCTCAAATGGTGCTCCTAATGCAGTCATAACCGCAAACAG

TAAGGGGAAAGTCGGTGAAAGCATTACATTTAGCAGTGAAAACA

GTACAGACCCAAACGGGAAGATCGTCAGCGTCTTATGGGACTTC

GGTGATGGCTCGACAAGTACACAAACCAAGCCGACGCACCAATA

TGGGAGTGAAGGGGAGTATTCGGTCAGCCTAAGTGTGACAGACA

GTGAAGGCTTGACGGCAACCGCCACTCATACTGTTGTTATCTCA

GCGTTGGGCGGTAATGACACATTGCCACAAGACTGCGCGGTGCA

AAGTAAAGTAAGCGGTGGGCGCTTAACAGCAGGAGAACCAGTTT

GCTTGGCAAATCAACAAACCATTTGGCTGAGCGTACCAGCGGTG

AATGAGAGCTCAAACCTGGCGATAACGACGGGGAATGGTACGGG

CAACCTAAAGCTTGAATACAGTAACTCTGGTTGGCCGGATGATA

CTAATCTTCACGGGTGGTCAGATAATATTGGTAATGGAGAGTGT

ATTACGTTGTCAAATCAGAGTAACTACTGGGGCTACGTTAAAGT

CTCTGGTGACTTTGAGAATGCCCCCATCGTCGTTGATTTTGATG

CTCAGAAGTGTCGTCAG, wherein Z is hydrogen.

21. An isolated and purified gene encoding a collagenase precursor of *Vibrio alginolyticus* which comprises a DNA sequence of the following formula as shown in SEQ ID No. 25:

Z—

ACTGCTTGTGATTTGGAGGCATTGGTTACCGAAAGCAGTAACCA

ATTGATCAGCGAAATTTTAAGTCAGGGCGCGACGTGTGTGAACC

AGTTATTCTCTGCTGAAAGTCGGATTCAAGAGTCGGTATTTACC

TCCGATCATATGTACAACATCGCTAAGCACACTACGACGTTGGC

GAAGGGGTATACGGGTGGCGGGAGCGATGAACTAGAAACGTTGT

TCTTATACTTACGCGCGGGTTATTACGCCGAGTTTTACAATGAC

AACATCTCATTTATTGAATGGGTCACCCCAGCGGTGAAAGAATC

AGTGGATGCGTTTGTTAACACAGCAAGCTTCTACGAGAACAGCG

ACCGTCACGGCAAAGTGCTTAGTGAGGTCATCATCACTATGGAT

AGTGCGGGCTTGCAGCACGCGTACTTACCGCAAGTGACCCAGTG

GCTTACTCGTTGGAATGATCAATACGCCCAGCACTGGTATATGC

GCAATGCGGTTAACGGTGTTTTCACTATTTTGTTTGGTGGGCAG

TGGAACGAGCAATTTGTGCAAATAATTGGCAACCAAACGGACCT

TGCCAAAGCTTTAGGCGATTTTGCTCTAAGGGCGTCATCAATCG

GTGCTGAAGATGAGTTTATGGCCCCGAATGCGGGGCGAGAGCTC

GGGCGTCTGACCAAGTATACGGCTAACGCGAGTTCTGTTGTGAA

GAGTCAGCTGAGTCGAATCTTTGAACAGTATGAAATGTATGGTC

GGGGTGACGCGGTTTGGCTTGCGGCGGCGGACACCGCCTCATAT

TACGCAGATTGTAGTGAGTTCGGAATTTGTAATTTCGAAACTGA

GCTAAAAGGCTTGGTGCTATCGCAAACTTATACTTGTAGCCCGA

CAATCCGAATTTTGTCTCAGAATATGACGCAAGAGCAACACGCG

GCCGCATGTTCTAAAATGGGTTACGAAGAGGGTTACTTTCATCA

GTCATTAGAAACTGGTGAACAGCCAGTAAAAGATGACCACAATA

CTCAGCTCCAAGTCAATATATTCGATTCAAGTACCGATTATGGT

AAGTACGCAGGGCCAATTTTCGATATTAGTACTGACAATGGCGG

TATGTACTTGGAGGGCGACCCTTCCCAGCCGGGGAATATTCCCA

ACTTTATTGCTTATGAACCCTCTTATGCGAACGCAGATCACTTT

GTCTGGAACTTAGAGCACGAATACGTGCATTACTTAGATGGTCG

ATTTGATCTCTATGGAGGGTTTAGTCATCCAACTGAAAAAAATAG

TGTGGTGGAGTGAAGGCATTGCAGAGTATGTCGCTCAAGAAAAT

GACAACCAAGCAGCACTTGAGACGATTCTAGACGGTTCGACATA

TACCTTAAGTGAGATTTTCGAGACTACTTATGATGGGTTTGATG

TCGATCGAATTTATCGTTGGGGGTACTTAGCTGTACGTTTTATG

TTTGAAAATCATAAAGATGACGTAAACCAAATGCTGGTGGAAAC

ACGCCAAGGGAATTGGATCAATTACAAGGCCACGATCACCCAAT

GGGCGAATTTGTATCAAAGTGAGTTTGAGCAGTGGCAGCAAACC

CTTGTCTCAAATGGTGCTCCTAATGCAGTCATAACCGCAAACAG

TAAGGGGAAAGTCGGTGAAAGCATTACATTTAGCAGTGAAAACA

GTACAGACCCAAACGGGAAGATCGTCAGCGTCTTATGGGACTTC

-continued
GGTGATGGCTCGACAAGTACACAAACCAAGCCGACGCACCAATA

TGGGAGTGAAGGGGAGTATTCGGTCAGCCTAAGTGTGACAGACA

GTGAAGGCTTGACGGCAACCGCCACTCATACTGTTGTTATCTCA

GCGTTGGGCGGTAATGACACATTGCCACAAGACTGCGCGGTGCA

AAGTAAAGTAAGCGGTGGGCGCTTAACAGCAGGAGAACCAGTTT

GCTTGGCAAATCAACAAACCATTTGGCTGAGCGTACCAGCGGTG

AATGAGAGCTCAAACCTGGCGATAACGACGGGGAATGGTACGGG

CAACCTAAAGCTTGAATACAGTAACTCTGGTTGGCCGGATGATA

CTAATCTTCACGGGTGGTCAGATAATATTGGTAATGGAGAGTGT

ATTACGTTGTCAAATCAGAGTAACTACTGGGGCTACGTTAAAGT

CTCTGGTGACTTTGAGAATGCCCCCATCGTCGTTGATTTTGATG

CTCAGAAGTGTCGTCAG, wherein Z is a DNA sequence of the formula:

ATGGAACTGAAGATTTTGAGTGTCGCGATTGCGACAACATTAAC

CAGCACTGGCGTATTTGCGTTAAGCGAGCCAGTTTCTCAAGTTA

CAGAGCAACATGCACATTCGGCTCATACACACGGTGTTGAATTC

AATCGAGTTGAATACCAACCAACCGCAACTCTCCCAATTCAGCC

CTCTAAGGCAACTCGAGTACAGTCACTTGAAAGCCTTGATGAGT

CGAGC.

22. A process for the production of a collagenase of *Vibrio alginolyticus* which comprises:
  inserting Bam HI linker into Hpa I site at Base No. 1213 on a DNA fragment of 7 kb composing the plasmid pLCO-1 of *Escherichia coli* JM 101 (FERM BP-3113) and inserting Sal I linker into Eco RV site at Base No. 3936 on the DNA fragment;
  cleaving said pLCO-1 containing the two linkers with Bam HI and Sal I to obtain a DNA fragment of 2.7 kb containing an entire collagenase gene;
  inserting said DNA fragment into Bam HI/Sal I site of a vector to obtain a recombinant plasmid;
  transforming *Escherichia coli* with said recombinant plasmid to obtain host cells;
  cultivating said host cells to express the collagenase; and
  recovering the collagenase.

* * * * *